United States Patent
Aoyama et al.

(10) Patent No.: US 10,548,316 B2
(45) Date of Patent: Feb. 4, 2020

(54) DIARYLAZOLE COMPOUND AND HARMFUL ORGANISM CONTROL AGENT

(71) Applicant: Nippon Soda Co., Ltd., Chiyoda-ku, Tokyo (JP)

(72) Inventors: Hikaru Aoyama, Odawara (JP); Maki Matsui, Odawara (JP); Keita Sakanishi, Odawara (JP); Takao Iwasa, Odawara (JP); Tomomi Kobayashi, Odawara (JP); Koichi Hirata, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 15/735,713

(22) PCT Filed: Jun. 17, 2016

(86) PCT No.: PCT/JP2016/068097
§ 371 (c)(1),
(2) Date: Dec. 12, 2017

(87) PCT Pub. No.: WO2016/204270
PCT Pub. Date: Dec. 22, 2016

(65) Prior Publication Data
US 2018/0160686 A1 Jun. 14, 2018

(30) Foreign Application Priority Data

Jun. 18, 2015 (JP) .................................. 2015-123323
Mar. 24, 2016 (JP) .................................. 2016-060604

(51) Int. Cl.
| | |
|---|---|
| *A01N 43/56* | (2006.01) |
| *A01N 43/653* | (2006.01) |
| *A01N 43/90* | (2006.01) |
| *A01N 47/18* | (2006.01) |
| *C07D 231/12* | (2006.01) |
| *C07D 231/16* | (2006.01) |
| *C07D 231/40* | (2006.01) |
| *C07D 401/04* | (2006.01) |
| *C07D 403/04* | (2006.01) |
| *C07D 249/06* | (2006.01) |

(52) U.S. Cl.
CPC .......... *A01N 43/56* (2013.01); *A01N 43/653* (2013.01); *A01N 43/90* (2013.01); *A01N 47/18* (2013.01); *C07D 231/12* (2013.01); *C07D 231/16* (2013.01); *C07D 231/40* (2013.01); *C07D 249/06* (2013.01); *C07D 401/04* (2013.01); *C07D 403/04* (2013.01)

(58) Field of Classification Search
CPC .... A01N 43/56; A01N 43/647; A01N 43/653; C07D 231/38; C07D 249/06; C07D 403/04

See application file for complete search history.

(56) References Cited

U.S. PATENT DOCUMENTS

| 2004/0157904 A1 | 8/2004 | Rudolph et al. |
| 2012/0190687 A1 | 7/2012 | Schwarz et al. |

FOREIGN PATENT DOCUMENTS

| CA | 2929393 A1 * | 5/2015 | ............. A01N 43/56 |
| CA | 2929393 A1 | 5/2015 | |
| JP | 2006-510728 A | 3/2006 | |
| JP | 2007-530690 A | 11/2007 | |
| WO | WO 01/07413 A1 | 2/2001 | |
| WO | WO-0107413 A1 * | 2/2001 | ............. A01N 43/56 |
| WO | WO 2005/097759 A1 | 10/2005 | |
| WO | WO 2010/136145 A1 | 12/2010 | |
| WO | WO 2015/144826 A1 | 10/2015 | |
| WO | WO 2016/113155 A1 | 7/2016 | |

OTHER PUBLICATIONS

Meegalla, S.K. et al. "Synthesis and GABA receptor potency of 3-thiomethyl-4-(hetero)aryl-5-amino-1-phenylpyrazoles" Bioorganic & Medicinal Chemistry Letters 14 (2004) 4949-4953 (Year: 2004).*
Chatterjee, N. et al. "An approach toward the syntheses of triazolo benzoxazines, triazolo quinoxalines, triazolo benzodiazepines, triazolo benzoxazepines, and triazolo benzothiazines via a simple and convenient protocol using basic alumina as solid support" Tetrahedron Letters 55 (2014) 2261-2265 (Year: 2014).*
International Search Report dated Sep. 20, 2016, in PCT/JP2016/068097.
Gloecklhofer et al., "Towards continuous junction (CJ) organic electronic devises: Fast and clean posst-polymerization modification by oxidation using dimehtyldioxirane (DMDO)," Reactive & Functional Polymers, Jan. 2015, 86:16-26.

(Continued)

*Primary Examiner* — Andrew S Rosenthal
(74) *Attorney, Agent, or Firm* — Foley & Lardner LLP

(57) ABSTRACT

The present invention provides a compound represented by formula (I), (in the formula, $A^1$ and $A^2$ each independently represents a carbon atom or a nitrogen atom; $X^1$ represents an unsubstituted or substituted C1-6 alkyl group or the like; n represents an integer of 0 to 4; $R^1$ represents an unsubstituted or substituted C1-6 alkylthio group or the like; $B^1$ and $B^4$ each independently represent a carbon atom, a nitrogen atom or the like; $R^2$ and $R^3$ each independently represent a hydrogen atom, a halogeno group or the like; Ar represents an unsubstituted or substituted C6-10 aryl group or the like) or a salt thereof, and a harmful organism control agent including thereof.

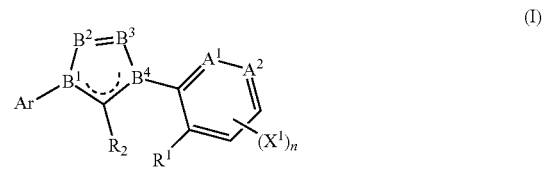

(I)

16 Claims, No Drawings

(56) References Cited

OTHER PUBLICATIONS

Hohloch et al., "Copper(I) Complexes of Normal and Abnormal Carbenes and Their Use as Catalysts for the Huisgen [3+2] Cycloaddition between Azides and Alkynes," European Journal of Inorganic Chemistry, 2011, 2011(20):3067-3075.

Meegalla et al. "Synthesis and GABA receptor potency of 3-thiomethyl-4-(hetero)aryl-5-amino-1-phenylpyrazoles," Bioorganic & Medicinal Chemistry Letters, 2004, 14(19):4949-4953.

Schweinfurth et al., "Heterobimetallic Cu-dppf (dppf=1,1'-Bis(diphenylphosphino)ferrocene) Complexes with 'Click' Derived Ligands: A Combined Structural, Electrochemical, Spectroelectrochemical, and Theoretical Study," Organometallics, 2013, 32(29):5834-5842.

Xu et al., "Copper-Catalyzed Trifluoromethylthiolation of Aryl Halides with Diverse Directing Groups," Organic Letters, 2014, 16(15):3942-3945.

\* cited by examiner

DIARYLAZOLE COMPOUND AND HARMFUL ORGANISM CONTROL AGENT

TECHNICAL FIELD

The present invention relates to a diarylazole compound and a harmful organism control agent. More specifically, the present invention relates to a diarylazole compound which has excellent insecticidal and/or acaricidal activity, is excellent in safety, and can be industrially and advantageously synthesized, and a harmful organism control agent including thereof as an active ingredient.

CROSS-REFERENCE TO RELATED APPLICATIONS

This application is a National Stage application of PCT/JP2016/068097, filed Jun. 17, 2016, which claims priority from Japanese Patent Application No. 2015-123323, filed Jun. 18, 2015, and Japanese Patent Application No. 2016-060604, filed Mar. 24, 2016, the content of which is incorporated herein by reference.

BACKGROUND ART

Various compounds having an acaricidal and/or insecticidal activity have been suggested. In order to practically use these compounds as an agrochemical, the compounds are required to have a sufficient effecacy, and also to have other properties such as being hard to cause drug-resistance, preventing phytotoxicity against the plants and soil combination, or having a low level of toxicity against livestocks, fishes or the like.

Patent Document 1 discloses a compound represented by formula (A). According to Patent Document 1, this compound is considered to be useful for treating diabetes, hyperglycemia, obesity, insulin resistance, arteriosclerosis, dyslipidemia, hypertension, and metabolic syndrome.

[Chemical formula 1]

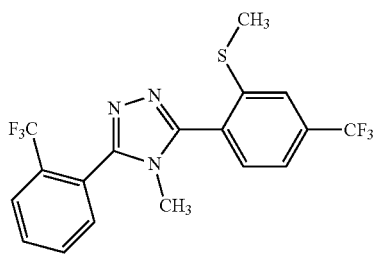

(A)

In Patent Document 2, a compound represented by formula (B) and the like are disclosed.

[Chemical formula 2]

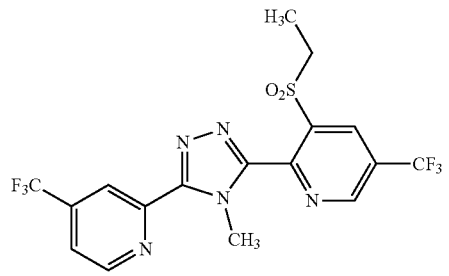

(B)

In Patent Document 3, a compound represented by formula (C) is disclosed. Patent Document 3 describes that this compound has insecticidal and acaricidal activities,

[Chemical formula 3]

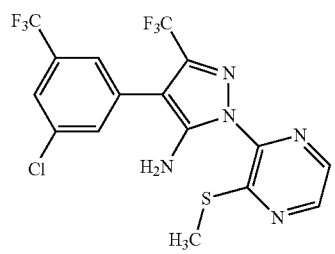

(C)

PRIOR ART LITERATURE

Patent Documents

Patent document 1: Japanese Unexamined Patent Application Publication (Translation of PCT Application) No. 2007-530690
Patent document 2: WO2015/144826 A1
Patent document 3: WO2010/136145 A1

DISCLOSURE OF INVENTION

Problems to be Solved by the Invention

An object of the present invention is to provide a diarylazole compound which is excellent in harmful organism control activity, particularly in insecticidal activity and/or acaricidal activity, excellent in safety, and can be synthesized industrially and advantageously. Another object of the present invention is to provide a harmful orgamin control agent including the same as an active ingredient. It is a further object of the present invention to provide an external parasite control agent, or an internal parasite control or extermination agent containing the same as an active ingredient.

Means for Solving the Problems

As a result of intensive studies to solve the above problems, the present invention including the following aspects has been completed.
[1] A compound represented by formula (I) or salt thereof.

[Chemical formula 4]

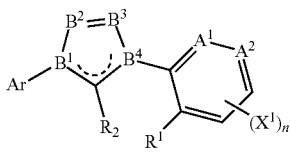

(I)

[in formula (I), $A^1$ and $A^2$ each independently represent a carbon atom or a nitrogen atom, provided that $A^1$ and $A^2$ are not nitrogen atoms simultaneously.

$X^1$ represents an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, formyl group, an unsubstituted or substituted C1-6 alkylcarbonyl group, an unsubstituted or substituted C1-6 alkoxycarbonyl group, mercapto group, an unsubstituted or substituted C1-6 alkylthio group, an unsubstituted or substituted C1-6 alkylsulfinyl group, an unsubstituted or substituted C1-6 alkylsulfonyl group, an unsubstituted or substituted aminocarbonyl group, an unsubstituted or substituted C3-8 cycloalkyl group, an unsubstituted or substituted C6-10 aryl group, an unsubstituted or substituted C6-10 aryloxy group, an unsubstituted or substituted 3- to 6-membered heterocyclyl group, an unsubstituted or substituted amino group, a halogeno group, a cyano group, or a nitro group.

n represents a number of $X^1$ and is an integer of 0 to 4. When n is 2 or more, $X^1$ may be the same as or different from each other.

$R^1$ is an unsubstituted or substituted C1-6 alkylthio group, an unsubstituted or substituted C1-6 alkylsulfinyl group, an unsubstituted or substituted C1-6 alkylsulfonyl group, an unsubstituted or a substituted or unsubstituted C1-6 alkylsulfonyloxy group, or a group represented by $-S(=O)(=N-R^a)-R^b$. Here, $R^a$ and $R^b$ each independently represent an unsubstituted or substituted C1-6 alkyl group.

$B^1$ and $B^4$ each independently represent a carbon atom or a nitrogen atom. $B^2$ and $B^3$ each independently represent a nitrogen atom or $CR^3$.

Here, when $B^1$ is a carbon atom, $B^2$ is a nitrogen atom or $CR^3$, and $B^3$ and $B^4$ are nitrogen atoms. When $B^1$ is a nitrogen atom, $B^2$ is a nitrogen atom, $B^3$ is a nitrogen atom or $CR^3$, and $B^4$ is a carbon atom.

$R^2$ and $R^3$ each independently represent a hydrogen atom, a halogeno group, a cyano group, an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, formyl group, an unsubstituted or substituted C1-6 alkylcarbonyl group, an unsubstituted or substituted C1-6 alkoxycarbonyl group, an unsubstituted or substituted amino group, an unsubstituted or substituted C1-6 alkylthio group, an unsubstituted or substituted C1-6 alkylsulfinyl group, an unsubstituted or substituted. C1-6 alkylsulfonyl group, an unsubstituted or substituted C1-6 alkylsulfonyloxy group, or a group represented by $-S(=O)(=N-R^a)-R^b$. Here, $R^a$ and $R^b$ each independently represent an unsubstituted or substituted C1-6 alkyl group. Here, $R^1$ and $R^2$ may bond together to form a divalent organic group.

Ar represents an unsubstituted or substituted. C6-10 aryl group or an unsubstituted or substituted 5- to 6-membered heteroaryl group.

[2] The compound or salt thereof according to [1], wherein formula (I) is formula (II) to formula (V).

[Chemical fomula 5]

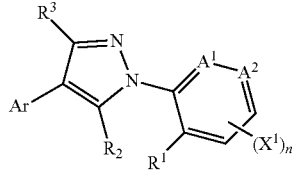

(II)

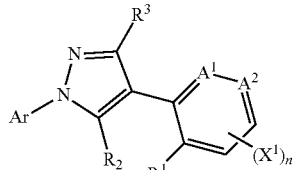

(III)

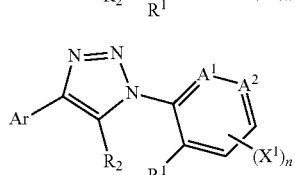

(IV)

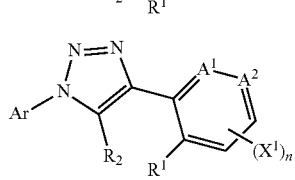

(V)

[In formula (IL), $A^1$, $A^2$, $X^1$, n, $R^1$, $R^2$, $R^3$ and Ar have the same meanings as those in formula (I).]

[3] A harmful organism control agent comprising at least one selected from the group consisting of the compounds and salts thereof defined in [1] or [2] as an active ingredient.

[4] An insecticide or acaricide comprising at least one selected from the group consisting of the compounds and salts thereof defined in [1] or [2] as an active ingredient.

[5] An external parasite control agent comprising at least one selected from the group consisting of the compounds and salts thereof defined in [1] or [2] as an active ingredient.

[6] An internal parasite control or extermination agent comprising at least one selected from the group consisting of the compounds and salts thereof defined in [1] or [2] as an active ingredient.

Effects of the Invention

The diarylazole compound of the present invention can control harmful organisms which are harmful to agricultural crops and cause problems in terms of hygiene. In particular, the diarylazole compound of the present invention can control various agricultural pests and acari effectively at a low concentration. Furthermore, the diarylazole compound of the present invention can effectively control external and internal parasites which are harmful to humans or animals.

BEST MODE FOR CARRYING OUT THE INVENTION

[Diarylazole Compound]

The diarylazole compound of the present invention is a compound represented by formula (I) (hereinafter, sometimes referred to as compound (I)) or a salt of compound (I).

[Chemical formula 6]

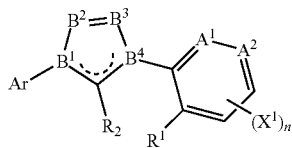

(I)

First of all, in the present invention, the term "unsubstituted" means that it is only a group to be a mother nucleus. When the term "having a substituent" is not mentioned and it is described only by the name of a group which is a mother nucleus, it means "unsubstituted" unless otherwise stated.

On the other hand, the term "having a substituent" means that any hydrogen atom of a group which constitutes a mother nucleus is substituted with a group having a structure the same as or different from the mother nucleus. Accordingly, the "substituent" is another group bonded to a group which is a mother nucleus. The number of substituents may be one, or two or more. Two or more substituents may be the same or different.

The term "C1-6" and the like mean that the number of carbon atoms in the mother nucleus is 1 to 6. The number of carbon atoms does not include the number of carbon atoms present in the substituents. For example, a butyl group having an ethoxy group as a substituent is classified as a C2 alkoxy C4 alkyl group.

"Substituent" is not particularly limited as long as it is chemically acceptable and has the effect of the present invention. The groups which can be "substituents" are exemplified below.

A C1-6 alkyl group such as a methyl group, ethyl group, n-propyl group, i-propyl group, n-butyl group, s-butyl group, i-butyl group, t-butyl group, n-pentyl group, n-hexyl group, or the like;

A C2-6 alkenyl group such as a vinyl group, 1-propenyl group, 2-propenyl group (allyl group), 1-butenyl group, 2-butenyl group, 3-butenyl group, 1-methyl-2-propenyl group, 2-methyl-2-propenyl group, or the like;

A C2-6 alkynyl group such as an ethynyl group, 1-propynyl group, 2-propynyl group, 1-butyryl group, 2-butynyl group, 3-butynyl group, 1-ethyl-2-propynyl group, or the like;

A C3-8 cycloalkyl group such as a cyclopropyl group, cyclobutyl group, cyclopentyl group, cyclohexyl group, cubanyl group, or the like;

A C6-10 aryl group such as a phenyl group, naphthyl group, or the like;

A C6-10 aryl C1-6 alkyl group such as a benzyl group, phenethyl group, or the like;

A 3- to 6-membered heterocyclyl group;

A 3- to 6-membered heterocyclyl C1-6 alkyl group;

A hydroxyl group;

A C1-6 alkoxy group such as a methoxy group, ethoxy group, n-propoxy group, i-propoxy group, n-butoxy group, s-butoxy group, i-butoxy group, t-butoxy group, or the like;

A C2-6 alkenyloxy group such as a vinyloxy group, allyloxy group, propenyloxy group, butenyloxy group, or the like;

A C2-6 alkynyloxy group such as an ethynyloxy group, propargyloxy group, or the like;

A C6-10 aryloxy group such as a phenoxy group and naphthoxy group; or the like;

A C6-10 aryl C1-6 alkoxy group such as a benzyloxy group, phenethyloxy group, or the like;

A 5 to 6-membered heteroaryloxy group such as a thiazolyloxy group, pyridyloxy group, or the like;

A 5- to 6-membered heteroaryl C1-6 alkyloxy group such as a thiazolylmethyloxy group and a pyridylmethyloxy group, or the like;

A formyl group;

A C1-6 alkylcarbonyl group such as an acetyl group, propionyl group, or the like;

A formyloxy group;

A C1-6 alkylcarbonyloxy group such as an acetyloxy group, propionyloxy group, or the like;

A C6-10 arylcarbonyl group such as a benzoyl group, or the like;

A C1-6 alkoxycarbonyl group such as a methoxycarbonyl group, ethoxycarbonyl group, n-propoxycarbonyl group, i-propoxycarbonyl group, n-butoxycarbonyl group, t-butoxycarbonyl group, or the like;

A C1-6 alkoxycarbonyloxy group such as a methoxycarbonyloxy group, ethoxycarbonyloxy group, n-propoxycarbonyloxy group, i-propoxycarbonyloxy group, n-butoxycarbonyloxy group, t-butoxycarbonyloxy group, or the like;

A carboxyl group;

A halogeno group such as a fluoro group, chloro group, bromo group, iodo group, or the like;

A C1-6 haloalkyl groups such as a chloromethyl group, chloroethyl group, trifluoromethyl group, 1,2-dichloro-n-propyl group, 1-fluoro-n-butyl group, perfluoro-n-pentyl group, or the like;

A C2-6 haloalkenyl group such as a 2-chloro-1-propenyl group, 2-fluoro-1-butenyl group, or the like;

A C2-6 haloalkynyl group such as a 4,4-dichloro-1-butynyl group, 4-fluoro-1-pentynyl group, 5-bromo-2-pentynyl group, or the like;

A C1-6 haloalkoxy group such as a trifluoromethoxy group, 2-chloro-n-propoxy group, 2,3-dichlorobutoxy group, or the like;

A C2-6 haloalkenyloxy group such as a 2-chloropropenyloxy group, 3-bromobutenyloxy group, or the like;

A C1-6 haloalkylcarbonyl group such as a chloroacetyl group, trifluoroacetyl group, trichloroacetyl group, or the like;

An amino group;

A C1-6 alkyl-substituted amino group such as a methylamino group, dimethylamino group, diethylamino group, or the like;

A C6-10 arylamino group such as an anilino group, naphthylamino group, or the like;

A C6-10 aryl C1-6 alkylamino group such as a benzylamino group, phenethylamino group, or the like;

A formylamino group;

A C1-6 alkylcarbonylamino group such as an acetylamino group, propanoylamino group, butyrylamino group, i-propylcarbonylamino group, or the like;

A mono C1-6 alkoxycarbonylamino group such as a methoxycarbonylamino group, ethoxycarbonylamino group, n-propoxycarbonylamino group, i-propoxycarbonylamino group, or the like;

A diC1-6 alkoxycarbonylamino group such as a di(methoxycarbonyl)amino group, di(ethoxycarbonyl)amino group, di(n-propoxycarbonyl)amino group, di(i-propoxycarbonyl)amino group, di (n-butoxycarbonyl) amino group, di(t-butoxycarbonyl)amino group, or the like;

An unsubstituted or substituted aminocarbonyl group such as an aminocarbonyl group, dimethylaminocarbonyl group, phenylaminocarbonyl group, N-phenyl-N-methylaminocarbonyl group, or the like;

An iminoC1-6 alkyl group such as an iminomethyl group, (1-imino)ethyl group, (1-imino)-n-propyl group, or the like;

An unsubstituted or substituted N-hydroxyimino C1-6 alkyl group such as an N-hydroxy-iminomethyl group, (1-(N-hydroxy)-imino)ethyl group, (1-(N-hydroxy)-imino) propyl group, N-methoxy-iminomethyl group, (1-(N-methoxy)-imino)ethyl group;

An aminocarbonyloxy group;

A C1-6 alkyl-substituted aminocarbonyloxy group such as an ethylaminocarbonyloxy group, dimethylaminocarbonyloxy group, or the like;

A mercapto group;

A C1-6 alkylthio group such as a methylthio group, ethylthio group, n-propylthio group, i-propylthio group, n-butylthio group, i-butylthio group, s-butylthio group, t-butylthio group, or the like;

A C1-6 haloalkylthio group such as trifluoromethylthio group, 2,2,2-trifluoroethylthio group, or the like;

A C6-10 arylthio group such as a phenylthio group, naphthylthio group, or the like;

A 5- to 6-membered heteroarylthio group such as a thiazolylthio group, pyridylthio group, or the like;

A C1-6 alkylsulfinyl group such as a methylsulfinyl group, ethylsulfinyl group, t-butylsulfinyl group, or the like;

A C1-6 haloalkylsulfinyl group such as a trifluoromethylsulfinyl group, 2,2,2-trifluoroethylsulfinyl group, or the like;

A C6-10 arylsulfinyl group such as a phenylsulfinyl group, or the like;

A 5- to 6-membered heteroarylsulfinyl group such as a thiazolylsulfinyl group, pyridylsulfinyl group, or the like;

A C1-6 alkylsulfonyl group such as a methylsulfonyl group, ethylsulfonyl group, t-butylsulfonyl group, or the like;

A C1-6 haloalkylsulfonyl group such as a trifluoromethylsulfonyl group 2,2-trifluoroethylsulfonyl group, or the like;

A C6-10 arylsulfonyl group such as a phenylsulfonyl group, or the like;

A 5- to 6-membered heteroarylsulfonyl group such as a thiazolylsulfonyl group, pyridylsulfonyl group, or the like;

A C1-6 alkylsulfonyloxy group such as a methylsulfonyloxy group, ethylsulfonyloxy group, t-butylsulfonyloxy group, or the like;

A C1-6 haloalkylsulfonyloxy group such as a trifluoromethylsulfonyloxy group, 2,2,2-trifluoromethylsulfonyloxy group, or the like;

A triC1-6 alkyl-substituted silyl group such as a trimethylsilyl group, triethylsilyl group, t-butyldimethylsilyl group, or the like;

A triC6-10 aryl-substituted silyl group such as a triphenylsilyl group;

A cyano group;

A nitro group;

Further, in these "substituents", any hydrogen atom in the substituents may be substituted with a group having a different structure. The "substituent" in that case includes a C1-6 alkyl group, a C1-6 haloalkyl group, a C1-6 alkoxy group, a C1-6 haloalkoxy group, a halogeno group, a cyano group, a nitro group and the like.

In addition, the above-described "3- to 6-membered heterocyclyl group" includes 1 to 4 hetero atoms selected from the group consisting of a nitrogen atom, an oxygen atom and a sulfur atom as constituent atoms of the ring. The heterocyclyl group may be either monocyclic or polycyclic. In the polycyclic heterocyclyl group, as long as at least one ring is a heterocyclic ring, the remaining rings may be any of a saturated alicyclic ring, an unsaturated alicyclic ring and an aromatic ring. Examples of the "3- to 6-membered heterocyclyl group" include a 3- to 6-membered saturated heterocyclyl group, a 5- to 6-membered heteroaryl group, a 5- to 6-membered partially unsaturated heterocyclyl group, and the like.

Examples of the "3- to 6-membered saturated heterocyclyl group" include an aziridinyl group, epoxy group, pyrrolidinyl group, tetrahydrofuranyl group, thiazolidinyl group, piperidyl group, piperazinyl group, morpholinyl group, dioxolanyl group, dioxanyl group, and the like.

Examples of the "5-membered heteroaryl group" include a pyrrolyl, furyl, thienyl, imidazolyl, pyrazolyl, oxazolyl, isoxazolyl, thiazolyl, isothiazolyl, triazolyl, oxadiazolyl, thiadiazolyl, tetrazolyl, and the like.

Examples of the "6-membered heteroaryl group" include a pyridyl group, pyrazinyl group, pyrimidinyl group, pyridazinyl group, triazinyl group, and the like.

[$A^1$, $A^2$]

In formula (I), $A^1$ and $A^2$ each independently represent a carbon atom or a nitrogen atom, provided that $A^1$ and $A^2$ are not nitrogen atoms simultaneously.

The carbon atoms in $A^1$ and $A^2$ may have a substituent. When $A^1$ or $A^2$ is a carbon atom, it means that $A^1$ or $A^2$ represents CH or $CX^1$. That is, the compound represented by formula (I) is a compound represented by one of formula (I-1) to formula (I-3).

[Chemical formula 7]

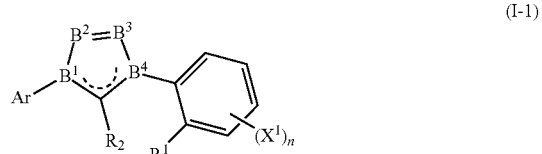

(I-1)

[Chemical formula 8]

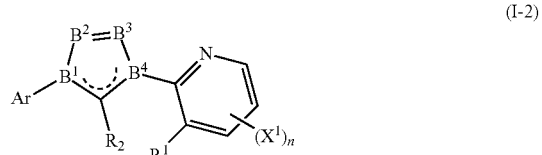

(I-2)

[Chemical formula 9]

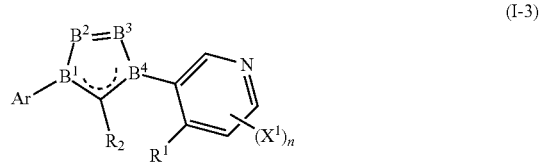

(I-3)

In formulas (I-1) to (I-3), $X^1$, n, $R^1$, $R^2$ and Ar have the same meanings as those in formula (I). Among the compounds, the compound represented by formula (I-1) or formula (I-2) is preferable.

[B¹, B², B³, B⁴]

B$^1$ and B$^4$ each independently represent a carbon atom or a nitrogen atom, and B$^2$ and B$^3$ each independently represent a nitrogen atom or CR$^3$. Here, when B$^1$ is a carbon atom, B$^2$ is a nitrogen atom or CR$^3$ and B$^3$ and B$^4$ are nitrogen atoms. When B$^1$ is a nitrogen atom, B$^2$ is a nitrogen atom, B$^3$ is a nitrogen atom or CR$^3$ and B$^4$ is a carbon atom.

That is, the compound represented by formula (I) is a compound represented by one of formula (II) to formula (V).

[Chemical formula 10]

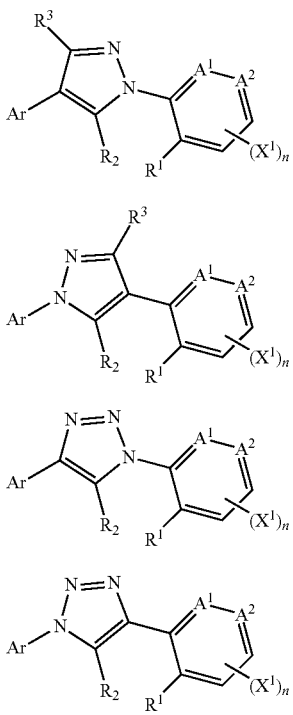

In formulas (II) to (V), A$^1$, A$^2$, R$^1$, R$^2$, X$^1$, n and Ar have the same meanings as those in formula (I). Among the compounds, the compound represented by formula (II) is preferable.

[X$^1$, n]

In formula (I), X$^1$ represents an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, a formyl group, an unsubstituted or substituted C1-6 alkylcarbonyl group, an unsubstituted or substituted C1-6 alkoxycarbonyl group, a mercapto group, an unsubstituted or substituted C1-6 alkylthio group, an unsubstituted or substituted C1-6 alkylsulfinyl group, an unsubstituted or substituted C1-6 alkylsulfonyl group, an unsubstituted or substituted aminocarbonyl group, an unsubstituted or substituted C3-8 cycloalkyl group, an unsubstituted or substituted C6-10 aryl group, an unsubstituted or substituted C6-10 aryloxy group, an unsubstituted or substituted 3- to 6-membered heterocyclyl group, an unsubstituted or substituted amino group, a halogeno group, a cyano group, or a nitro group.

The "C1-6 alkyl group" for X$^1$ may be a straight chain or a branched chain if it has 3 or more carbon atoms. Examples of the "alkyl group" include a methyl group, ethyl group, n-propyl group, n-butyl group, n-pentyl group, n-hexyl group, i-propyl group, i-butyl group, s-butyl group, t-butyl group, i-pentyl group, neopentyl group, 2-methyl butyl group, 2,2-dimethyl propyl group, i-hexyl group, and the like.

Specific examples of the "substituted C1-6 alkyl group" include a C1-6 haloalkyl group such as a fluoromethyl group, chloromethyl group, bromomethyl group, difluoromethyl group, dichloromethyl group, dibromomethyl group, trifluoromethyl group, trichloromethyl group, tribromomethyl group, 1-chloroethyl group, 2,2,2-trifluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethylethyl group, perfluorohexyl group, perchlorohexyl group, 2,4,6-trichlorohexyl group, or the like;

a C1-6 alkoxy C1-6 alkyl group such as a methoxymethyl group, ethoxymethyl group, methoxyethyl group, ethoxyethyl group, methoxy-n-propyl group, n-propoxymethyl group, i-propoxyethyl group, s-butoxymethyl group, t-butoxyethyl group, or the like;

a C6-10 aryl C1-6 alkyl group such as a benzyl group, phenethyl group, or the like;

a C3-8 cycloalkyl C1-6 alkyl group such as a cyclopropylmethyl group, 2-cyclopropylethyl group, cyclopentylmethyl group, 2-cyclohexylethyl group, 2-cyclooctylethyl group, or the like; and the like.

Examples of the "C2-6 alkenyl group" for X$^1$ include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, methyl-2-butenyl group, 1-hexenyl group, 2-hexenyl group, 3-hexenyl group, 4-hexenyl group, 5-hexenyl group, and the like.

Specific examples of the "substituted C2-6 alkenyl group" include a C2-6 haloalkenyl group such as a 2-chloro-1-propenyl group, 2-fluoro-1-butenyl group, or the like;

a C1-6 alkoxy C2-6 alkenyl group such as a 2-n-butoxyvinyl group, 1-ethoxy-vinyl group, or the like; and the like.

Examples of the "C2-6 alkynyl group" for X$^1$ include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group and the like.

Specific examples of the "substituted C2-6 alkynyl group" include a C2-6 haloalkynyl group such as a 4,4-dichloro-1-butynyl group, 4-fluoro-1-pentynyl group, 5-bromo-2-pentynyl group, and the like.

Examples of the "C1-6 alkoxy group" for X$^1$ include a methoxy group, ethoxy group, n-propoxy group, n-butoxy group, n-pentyloxy group, n-hexyloxy group, i-propoxy group, i-butoxy group, s-butoxy group, t-butoxy group, i-hexyloxy group, and the like.

Specific examples of the "substituted C1-6 alkoxy group" include a C1-6 haloalkoxy group such as a chloromethoxy group, dichloromethyl group, difluoromethoxy group, trichloromethoxy group, trifluoromethoxy group, 1-fluoroethoxy group, 1,1-difluoro-ethoxy group, 2,2,2-trifluoroethoxy group, pentafluoroethoxy group, 2,2,3,4,4,4-hexafluoro-butoxy group, or the like;

a C1-6 alkoxy C1-6 alkoxy group such as a methoxymethoxy group, methoxy ethoxy group, or the like;

a C6-10 aryl C1-6 alkoxy group such as a benzyloxy group, phenethyloxy group, or the like;

a C3-8 cycloalkyl C1-6 alkoxy group such as a cyclopropylmethyloxy group, or the like; and the like.

Examples of the "C1-6 alkylcarbonyl group" for $X^1$ include an acetyl group, propionyl group, and the like.

Specific examples of the "substituted C1-6 alkylcarbonyl group" include a C1-6 haloalkylcarbonyl group such as a chloroacetyl group, trifluoroacetyl group, trichloroacetyl group, or the like; and the like.

Examples of the "C1-6 alkoxycarbonyl group" for $X^1$ include a methoxycarbonyl group, ethoxycarbonyl group, n-propoxycarbonyl group, i-propoxycarbonyl group, t-butoxycarbonyl group, and the like.

Specific examples of the "substituted C1-6 alkoxycarbonyl group" include a C1-6 haloalkoxycarbonyl group such as a fluoromethoxycarbonyl group, chloromethoxycarbonyl group, bromomethoxycarbonyl group, difluoromethoxycarbonyl group, dichloromethoxycarbonyl group, dibromomethoxycarbonyl group, trifluoromethoxycarbonyl group, trichloromethoxycarbonyl group, tribromomethoxycarbonyl group, 2,2,2-trifluoroethoxycarbonyl group, or the like;

a C3-8 cycloalkyl C1-6 alkoxycarbonyl group such as a cyclopropylmethoxycarbonyl group, cyclobutylmethoxycarbonyl group, cyclopentylmethoxycarbonyl group, cyclohexylmethoxycarbonyl group, 2-cyclopropylethoxycarbonyl group, or the like; and the like.

Examples of the "C1-6 alkylthio group" for $X^1$ include a methyl thio group, ethyl thio group, n-propyl thio group, n-butyl thio group, n-pentyl thio group, n-hexyl thio group, i-propyl thio group, i-butyl thio group, and the like.

Specific examples of the "substituted C1-6 alkylthio group" include a C1-6 haloalkylthio group such as a trifluoromethylthio group, 2,2,2-trifluoroethylthio group, or the like; and the like.

Examples of the "C1-6 alkylsulfinyl group" for $X^1$ include a methylsulfinyl group, ethylsulfinyl group, t-butylsulfinyl group, and the like.

Specific examples of the "substituted C1-6 alkylsulfinyl group" include a C1-6 haloalkylsulfinyl group such as trifluoromethylsulfinyl group, 2,2,2-trifluoroethylsulfinyl group, or the like.

Examples of the "C1-6 alkylsulfonyl group" for $X^1$ include a methylsulfonyl group, ethylsulfonyl group, t-butylsulfonyl group, and the like.

Specific examples of the "substituted C1-6 alkylsulfonyl group" include a C1-6 haloalkylsulfonyl group such as a trifluoromethylsulfonyl group, 2,2,2-trifluoroethylsulfonyl group, or the like.

Preferred examples of the substituents on the "C1-6 alkyl group", "C2-6 alkenyl group", "C2-6 alkynyl group", "C1-6 alkoxy group", "C1-6 alkyl carbonyl group", "C1-6 alkoxycarbonyl group", "C1-6 alkyl thio group", "C1-6 alkyl sulfinyl group", and "C1-6 alkyl sulfonyl group" for $X^1$ include a C1-6 alkoxy group, a halogeno group, a cyano group, a C3-8 cycloalkyl group, a C6-10 aryl group, a 3- to 6-membered heterocyclyl group, and the like.

Examples of the "C3-8 cycloalkyl group" for $X^1$ include a cyclopropyl group, cyclobutyl group, cyclopentyl group, cyclohexyl group, cycloheptyl group, and the like.

The "C6-10 aryl group" for $X^1$ may be either a single ring or a polycyclic ring. In the polycyclic aryl group, as long as at least one ring is an aromatic ring, the remaining rings may be any of a saturated alicyclic ring, an unsaturated alicyclic ring and an aromatic ring.

Examples of the "C6-10 aryl group" include a phenyl group, naphthyl group, azulenyl group, indenyl group, indanyl group, tetralinyl group, and the like.

Examples of the "C6-10 aryloxy group" for $X^1$ include a phenoxy group, naphthoxy group, and the like.

The "3- to 6-membered heterocyclyl group" for $X^1$ includes 1 to 4 hetero atoms selected from the group consisting of a nitrogen atom, an oxygen atom and a sulfur atom as constituent atoms of the ring. The heterocyclyl group may be either monocyclic or polycyclic. In the polycyclic heterocyclyl group, as long as at least one ring is a heterocyclic ring, the remaining rings may be any of a saturated alicyclic ring, an unsaturated alicyclic ring and an aromatic ring. Examples of the "3- to 6-membered heterocyclyl group" include a 3- to 6-membered saturated heterocyclyl group, a 5- to 6-membered heteroaryl group, a 5- to 6-membered partially unsaturated heterocyclyl group, and the like.

Examples of the "3- to 6-membered saturated heterocyclyl group" include an aziridinyl group, epoxy group, pyrrolidinyl group, tetrahydrofuranyl group, thiazolidinyl group, piperidyl group, piperazinyl group, morpholinyl group, dioxolanyl group (more specifically, [1,3]dioxanyl group), dioxanyl group (more specifically, [1,3]dioxanyl group or [1,4]dioxanyl group), and the like. The preferable example is a 5- to 6-membered saturated heterocyclyl group.

Examples of the "5-membered heteroaryl group" include a pyrrolyl group, furyl group, thienyl group, imidazolyl group, pyrazolyl group, oxazolyl group, isoxazolyl group, thiazolyl group, isothiazolyl group, triazolyl group (more specifically, [1,2,3]triazolyl group, or [1,2,4]triazolyl group), oxadiazolyl group (more specifically, [1,2,4]oxadiazolyl group, or [1,3,4]oxadiazolyl group), thiadiazolyl group, tetrazolyl group, and the like.

Examples of the "6-membered heteroaryl group" include a pyridyl group, pyrazinyl group, pyrimidinyl group, pyridazinyl group, triazinyl group, and the like.

Examples of the "partially unsaturated 5-membered heterocyclyl group" include a pyrrolinyl group, imidazolinyl group (dihydroimidazolyl group), pyrazolinyl group, oxazolinyl group, isoxazolinyl group, thiazolinyl group, and the like.

Examples of the "partially unsaturated 6-membered heterocyclyl group" include a thiopyranyl group, 2H-pyridin-1-yl group, 4H-pyridin-1-yl group, and the like.

As the "3- to 6-membered heterocyclyl group", a 5-membered heteroaryl group is preferable, and a pyrazolyl group or a triazolyl group is more preferable, and a triazolyl group (more preferably, a [1,2,4]triazolyl group) is particularly preferable.

Examples of the substituents on the "C3-8 cycloalkyl group", "C6-10 aryl group", "C6-10 aryloxy" and "3- to 6-membered heterocyclyl group" for $X^1$ include a C1-6 alkyl group, a C1-C6 haloalkyl group, a hydroxyl group, a C1-6 alkoxy group, a C1-6 alkoxycarbonyl group, a C1-6 alkylthio group, a C1-6 alkylsulfinyl group, a C1-6 alkylsulfonyl group, an amino group, a C1-6 alkyl-substituted amino group, a halogeno group, a cyano group, a nitro group, and the like. Among these examples, a C1-6 alkyl group, a C1-6 haloalkyl group, a hydroxyl group, a C1-6 alkoxy group, a halogeno group, a cyano group and a nitro group are preferable.

Examples of the "substituted amino group" for $X^1$ include a C1-6 alkyl-substituted amino group such as a methylamino group, n-butylamino group, dimethylamino group, diethylamino group, or the like;

a mono C1-6 alkoxycarbonylamino group such as a methoxycarbonylamino group, ethoxycarbonylamino group, n-propoxycarbonylamino group, i-propoxycarbonylamino group, t-butoxyaminocarbonylamino group, or the like;

a diC1-6 alkoxycarbonylamino group such as a dimethoxycarbonylamino group, diethoxycarbonylamino group, di-i-propoxycarbonylamino group, di-n-propoxycarbonylamino group, di-t-butoxyaminocarbonylamino group, or the like; and the like.

Specific examples of the "substituted aminocarbonyl group" for $X^1$ include a C1-6 alkyl-substituted aminocarbonyl group such as a methylaminocarbonyl group, ethylaminocarbonyl group, dimethylaminocarbonyl group, diethylaminocarbonyl group, or the like.

Examples of the "halogeno group" for $X^1$ include a fluoro group, chloro group, bromo group, iodo group, and the like.

Among the above groups, $X^1$ is preferably a C1-6 haloalkyl group or an unsubstituted or substituted 3- to 6-membered heterocyclyl group.

In formula (I), n represents a chemically acceptable number of $X^1$ and is an integer of 0 to 4. When n is 2 or more, $X^1$ may be the same as or different from each other. Incidentally, when either $A^1$ or $A^2$ is a nitrogen atom, the upper limit of the chemically acceptable number of $X^1$ is 3.

n is preferably 0 to 2, and more preferably 1.

[$R^1$]

In formula (I), $R^1$ represents an unsubstituted or substituted C1-6 alkylthio group, an unsubstituted or substituted C1-6 alkylsulfinyl group, an unsubstituted or substituted C1-6 alkylsulfonyl group, an unsubstituted or substituted C1-6 alkylsulfonyloxy group, or a group represented by formula: —S(=O)(=N—$R^a$)—$R^b$. Here, $R^a$ and $R^b$ each independently represent an unsubstituted or substituted C1-6 alkyl group.

Examples of the "C1-6 alkylthio group", "C1-6 alkylsulfinyl group", "C1-6 alkylsulfonyl group" and the groups having substituents on these groups for $R^1$ are the same as those exemplified for $X^1$ above.

Examples of the "C1-6 alkylsulfonyloxy group" for $R^1$ include a methylsulfonyloxy group, ethylsulfonyloxy group, t-butylsulfonyloxy group and the like.

Specific examples of the "substituted C1-6 alkylsulfonyloxy group" include a C1-6 haloalkylsulfonyloxy group such as a trifluoromethylsulfonyloxy group, 2,2,2-trifluoroethylsulfonyloxy group, and the like.

Examples of the "C1-6 alkyl group" and the groups having substituents on the group for $R^a$ and $R^b$ in the group represented by formula: —S(=O)(=N—$R^a$)—$R^b$ are the same as those exemplified for $X^1$ above.

$R^1$ is preferably a C1-6 alkylthio group, a C1-6 alkylsulfinyl group, a C1-6 alkylsulfonyl group, and particularly preferably a C1-6 alkylsulfonyl group.

[$R^2$, $R^3$]

In formula (I), $R^2$ and $R^3$ each independently represent a hydrogen atom, a halogeno group, a cyano group, an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, a formyl group, an unsubstituted or substituted C1-6 alkylcarbonyl group, an unsubstituted or substituted C1-6 alkoxycarbonyl group, an unsubstituted or substituted amino group, an unsubstituted or substituted C1-6 alkylthio group, an unsubstituted or substituted alkylsulfinyl group, an unsubstituted or substituted C1-6 alkylsulfonyl group, an unsubstituted or substituted C1-6 alkylsulfonyloxy group, or a group represented by formula: —S(=O)(=N—$R^a$)—$R^b$. Here, $R^a$ and $R^b$ each independently represent an unsubstituted or substituted C1-6 alkyl group.

The "C1-6 alkyl group", "C2-6 alkenyl group", "C2-6 alkynyl group", "C1-6 alkoxy group", "C1-6 alkylcarbonyl group", "C1-6 alkoxy Carbonyl group", "C1-6 alkylthio group", "alkylsulfinyl group", "C1-6 alkylsulfonyl group", "C1-6 alkylsulfonyloxy group" and the groups having substituents on these groups for $R^2$ and $R^3$ are the same as those exemplified for $X^1$ or $R^1$ above.

The "C1-6 alkyl group" and the groups having substituents on these groups for $R^a$ and $R^b$ in the group represented by formula: —S(=O)(=N—$R^a$)—$R^b$ are the same as those exemplified for $X^1$ above.

Examples of the substituent on the "substituted amino group" for $R^2$ include a C1-6 alkyl group, a C1-6 alkoxy group and a 1-6 alkoxycarbonyl group.

Examples of the "substituted amino group" for $R^3$ are the same as those exemplified for $X^1$.

$R^2$ is preferably a hydrogen atom, an unsubstituted or substituted amino group, a C1-6 alkyl group, a halogeno group or a cyano group, and more preferably an unsubstituted or substituted amino group (preferably substituted with a C1-6 alkyl group, a C1-6 alkoxy group, a C1-6 alkoxycarbonyl group) and a C1-6 alkyl group.

$R^3$ is preferably a hydrogen atom or a C1-6 alkyl group, and more preferably a hydrogen atom.

$R^1$ and $R^2$ may bond together to form a divalent organic group. Examples of the divalent organic group formed by bonding $R^1$ and $R^2$ include —SO$_2$CH$_2$—, —SO$_2$CH(CH$_3$)—, —SOCH$_2$—, —SOCH(CH$_3$)—, —SCH$_2$—, —SCH(CH$_3$)—, and the like.

In formula (I), Ar represents an unsubstituted or substituted C6-10 aryl group or an unsubstituted or substituted 5- to 6-membered heteroaryl group.

Examples of the "C6-10 aryl group" and "5- to 6-membered heteroaryl group" for Ar are the same as those exemplified for $X^1$ above.

The "C6-10 aryl group" for Ar is preferably a phenyl group.

The "5- to 6-membered heteroaryl group" for Ar is preferably a thienyl group, pyrazolyl group, thiazolyl group, pyridyl group, pyrimidyl group or pyridazinyl group, and more preferably a pyridyl group or pyrazolyl group, and more preferably a pyridin-3-yl group or 1H-pyrazol-1-yl group.

Examples of the substituents on the "C6-10 aryl group" and "5- to 6-membered heteroaryl group" for Ar include an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, a formyl group, an unsubstituted or substituted C1-6 alkylcarbonyl group, an unsubstituted or substituted C1-6 alkoxycarbonyl group, a mercapto group, an unsubstituted or substituted C1-6 alkylthio group, an unsubstituted or substituted C1-6 alkylsulfinyl group, an unsubstituted or substituted C1-6 alkylsulfonyl group, an unsubstituted or substituted C3-8 cycloalkyl group, an unsubstituted or substituted C6-10 aryl group, an unsubstituted or substituted 3- to 6-membered heterocyclyl group, an unsubstituted or substituted pyridyloxy group, an unsubstituted or substituted amino group, a halogeno group, a cyano group, a nitro group, and the like.

Examples of the "C1-6 alkyl group", "C2-6 alkenyl group", "C2-6 alkenyl group", "C2-6 alkynyl group", "C1-6 alkoxy group", "C1-6 alkylcarbonyl group", "C1-6 alkoxycarbonyl group", "C1-6 alkylthio group" "C1-6 alkylsulfinyl group", "C1-6 alkylsulfonyl group", "C3-8 cycloalkyl group", "C6-10 aryl group", "3- to 6-membered heterocyclyl group", "amino group", "halogeno group" and the groups having substituents on these groups as the substituents on the "C6-10 aryl group" and "5- to 6-membered heteroaryl group" for Ar are the same as those exemplified for $X^1$ above.

The substituents on the "C6-10 aryl group" and "5- to 10-membered heteroaryl group" for Ar is preferably a C1-6 alkyl group, a C1-6 haloalkyl group, a C1-6 alkoxy group, a C1-6 haloalkoxy group, C1-6 alkylthio group, C1-6 haloalkylthio group, C1-6 alkylsulfinyl group, C1-6 haloalkylsulfinyl group, C1-6 alkylsulfonyl group, C1-6 haloalkylsulfonyl group, halogeno group or an (optionally a halogeno group- or a C1-6 haloalkoxy group-substituted) 5- to 6-membered heteroaryl group (preferably a pyridyl group), and more preferably a C1-6 alkyl group, a C1-6 haloalkyl group, a C1-6 haloalkoxy group, a C1-6 haloalkylthio group and a halogeno group.

The number of substituents on the "C6-10 aryl group" and "5- to 10-membered heteroaryl group" for Ar is preferably 0 to 3, more preferably 0 to 2, still more preferably 1 or 2.

There are no particular limitations on the salt of compound (I), provided that it is an agriculturally and horticulturally acceptable salt. Examples of the salt include salts of inorganic acids such as a hydrochloric acid, sulfuric acid or the like; salts of organic acids such as an acetic acid, lactic acid or the like; salts of alkaline metals such as a lithium, sodium, potassium or the like; salts of alkaline earth metals such as a calcium, magnesium or the like; salts of transition metals such as an iron, copper or the like; salts of organic bases such as an ammonia, triethylamine, tributylamine, pyridine, hydrazine or the like; and the like.

The compound (I) or salt thereof is not particularly limited by the production method thereof. For example, compound (I) or salt thereof may be obtained by a well-known production method described in the working examples or the like. In addition, the salt of compound (I) may be produced from compound (I) by a well-known method.

The diarylazole compound of the present invention has a superior effect for preventing harmful organisms such as various agricultural pests affecting the plant growth, acari or the like.

In addition, the diarylazole compound of the present invention has a high safety because it does not have phytotoxicity against plants and has a low level of toxicity against fishes or warm-blooded animals. Therefore, the diarylazole compound of the present invention is useful for an active ingredient of pesticide or acaricide.

Moreover, in recent years, many pests such as diamondback moths, planthoppers, leafhoppers and aphids have developed a resistance to the organic phosphorous agents and carbamate agents, and because of this, the efficacy of the traditional agrochemicals has become insufficient, new agrochemicals that are effective even for preventing the resistant strains of pests are desired. The diarylazole compound of the present invention demonstrates superior efficacy for preventing the sensitive strains of pests, and also for preventing the various resistant strains of pests and acaricide-resistant strains of acari.

The diarylazole compound of the present invention has a superior effect for preventing the external and internal parasites that are harmful to humans and animals. Moreover, the diarylazole compound of the preset invention is a highly safe compound, because it has a low level of toxicity to the fishes or warm-blooded animals. Therefore, the diarylimidazle compound of the present invention is useful as an active ingredient of external and internal parasite control agent.

In addition, the diarylazole compound of the present invention is effective for preventing the targeted organisms in any development stages, for example, acari and insect in the stages of eggs, nymph, larvae, pupa and adult.

[Harmful Organism Control Agent, Insecticide or Acaricide]

The harmful organism control agent, insecticide or acaricide of the present invention include at least one compound of the diarylazole compound of the present invention as an active ingredient. The amount of the diarylazole compound included in the harmful organism control agent, insecticide or acaricide of the present invention is not particularly limited as long as it demonstrates prevention effects against the harmful organisms.

The harmful organism control agent, insecticide or acaricide of the present invention are preferably used for crops; green stuff; edible roots; tuber crops; froot trees; trees of tea, coffee, cacao or the like; grasses for pastures; grasses for lawns; plants such as cotton; or the like.

As for the application to the plants, the harmful organism control agent, insecticide or acaricide of the present invention may be applied on any one part of the plants, such as leaf, stem, stalk, flower, bud, fruit, seed, sprout, root, tuber, tuberous root, shoot, cutting and the like. In addition, although the plant varieties for which the harmful organism control agent, insecticide or acaricide of the present invention is applicable are not particularly limited, examples of the plant varieties include the originals, varieties, improved varieties, cultivated varieties, mutant plants, hybrid plants, genetically-modified plants (GMO) and the like.

The harmful organism control agent of the present invention can be used for preventing various agricultural pests and acari by seed treatment, foliar spraying, soil application or water surface application and the like.

Specific examples of the various agricultural pests and acari which can be prevented by the harmful organism control agent of the present invention include the followings.

(1) Butterfly or Moth of Lepidoptera Order (a) moth belonging to the Arctiidae family, for example, *Hyphantria cunea, Lemyra imparilis;*

(b) moth belonging to the Bucculatricidae family, for example, *Bucculatrix pyrivorella;*

(c) moth belonging to the Carposinidae family, for example, *Carposina sasakii;*

(d) moth belonging to the Crambidae family, for example, *Diaphania* indica and *Diaphania nitidalis* of *Diaphania* spp.; for example, *Ostrinia furnacalis, Ostrinia nubilalis* and *Ostrinia scapulalis* of *Ostrinia* spp.; Others such as *Chilo suppressalis, Cnaphalocrocis medinalis, Conogethes punctiferalis, Diatraea grandiosella, Glyphodes pyloalis, Hellula undalis, Parapediasia teterrella;*

(e) moth belonging to the Gelechiidae family, for example, *Helcystogramma triannulella, Pectinophora gossypiella, Phthorimaea operculella, Sitotroga cerealella;*

(f) moth belonging to the Geometridae family, for example, *Ascotis selenaria;*

(g) moth belonging to the Gracillariidae family, for example, *Caloptilia theivora, Phyllocnistis citrella, Phyllonorycter ringoniella;*

(h) butterfly belonging to the Hesperiidae family, for example, *Parnara guttata;*

(i) moth belonging to the Lasiocampidae family, for example, *Malacosoma neustria;*

(j) moth belonging to the Lymantriidae family, for example, *Lymantria dispar* and *Lymantria monacha* of *Lymantria* spp.; Others such as *Euproctis pseudoconspersa*, *Orgyia thyellina*;

(k) moth belonging to the Lyonetiidae family, for example, *Lyonetia clerkella* and *Lyonetia prunifoliella malinella* of *Lyonetia* spp.;

(l) moth belonging to the Noctuidae family, for example, *Spodoptera depravata*, *Spodoptera eridania*, *Spodoptera exigua*, *Spodoptera frugiperda*, *Spodoptera littoralis* and *Spodoptera litura* of *Spodoptera* spp.; for example, *Autographa gamma* and *Autographa nigrisigna* of *Autographa* spp.; for example, *Agrotis ipsilon* and *Agrotis segetum* of *Agrotis* spp.; for example, *Helicoverpa armigera*, *Helicoverpa assulta* and *Helicoverpa zea* of *Helicoverpa* spp.; for example, *Heliothis armigera* and *Heliothis virescens* of *Heliothis* spp.; Others such as *Aedia leucomelas*, *Ctenoplusia agnata*, *Eudocima tyrannus*, *Mamestra brassicae*, *Mythimna separata*, *Naranga aenescens*, *Panolis japonica*, *Peridroma saucia*, *Pseudoplusia includens*, *Trichoplusia ni*;

(m) moth belonging to the Nolidae family, for example, *Earias insulana*;

(n) butterfly belonging to the Pieridae family, for example, *Pieris brassicae* and *Pieris rapae crucivora* of *Pieris* spp.;

(o) moth belonging to the Plutellidae family, for example, *Acrolepiopsis sapporensis* and *Acrolepiopsis suzukiella* of *Acrolepiopsis* spp.; others such as *Plutella xylostella*;

(p) moth belonging to the Pyralidae family, for example, *Cadra cautella*, *Elasmopalpus lignosellus*, *Etiella zinckenella*, *Galleria mellonella*;

(q) moth belonging to the Sphingidae, for example, *Manduca quinquemaculata* and *Manduca sexta* of *Manduca* spp.;

(r) moth belonging to the Stathmopodidae family, for example, *Stathmopoda masinissa*;

(s) moth belonging to the Tineidae family, for example, *Tinea translucens*;

(t) moth belonging to the Tortricidae family, for example, *Adoxophyes honmai* and *Adoxophyes orana* of *Adoxophyes* spp.; for example, *Archips breviplicanus* and *Archips fuscocupreanus Archips* spp.; others such as *Choristoneura fumiferana*, *Cydia pomonella*, *Eupoecilia ambiguella*, *Grapholitha molesta*, *Homona magnanima*, *Leguminivora glycinivorella*, *Lobesia botrana*, *Matsumuraeses phaseoli*, *Pandemis heparana*, *Sparganothis pilleriana*;

(u) moth belonging to the Yponomeutidae family, for example, *Argyresthia conjugella*.

(2) Pest of Thysanoptera Order (a) pest belonging to the Phlaeothripidae family, for example, *Ponticulothrips diospyrosi*;

(b) pest belonging to the Thripidae family, for example, *Frankliniella intonsa* and *Frankliniella occidentalis* of *Frankliniella* spp.; for example, *Thrips palmi* and *Thrips tabaci* of *Thrips* spp.; others such as *Heliothrips haemorrhoidalis*, *Scirtothrips dorsalis*.

(3) Pest of Hemiptera Order (A) Archaeorrhyncha Suborder (a) pest belonging to the Delphacidae family, for example, *Laodelphax striatella*, *Nilaparvata lugens*, *Perkinsiella saccharicida*, *Sogatella furcifera*.

(B) Clypeorrhyncha Suborder (a) pest belonging to the Cicadellidae family, for example, *Empoasca fabae*, *Empoasca nipponica*, *Empoasca onukii* and *Empoasca sakaii* of *Empoasca* spp.; others such as *Arboridia apicalis*, *Balclutha saltuella*, *Epiacanthus stramineus*, *Macrosteles striifrons*, *Nephotettix cinctinceps*.

(C) Heteroptera Suborder (a) pest belonging to the Alydidae family, for example, *Riptortus clavatus*;

(b) pest belonging to the Coreidae family, for example, *Cletus punctiger*, *Leptocorisa chinensis*;

(c) pest belonging to the Lygaeidae family, for example, *Blissus leucopterus*, *Cavelerius saccharivorus*, *Togo hemipterus*;

(d) pest belonging to the Miridae family, for example, *Halticus insularis*, *Lygus lineolaris*, *Psuedatomoscelis seriatus*, *Stenodema sibiricum*, *Stenotus rubrovittatus*, *Trigonotylus caelestialium*;

(e) pest belonging to the Pentatomidae family, for example, *Nezara antennata* and *Nezara viridula* of *Nezara* spp.; for example, *Eysarcoris aeneus*, *Eysarcoris lewisi* and *Eysarcoris ventralis* of *Eysarcoris* spp.; others such as *Dolycoris baccarum*, *Eurydema rugosum*, *Glaucias subpunctatus*, *Halyomorpha halys*, *Piezodorus hybneri*, *Plautia crossota*, *Scotinophora lurida*;

(f) pest belonging to the Pyrrhocoridae family, for example, *Dysdercus cingulatus*;

(g) pest belonging to the Rhopalidae family, for example, *Rhopalus msculatus*;

(h) pest belonging to the Scutelleridae family, for example, *Eurygaster integriceps*;

(i) pest belonging to the Tingidae family, for example, *Stephanitis nashi*.

(D) Sternorrhyncha Suborder (a) pest belonging to the Adelgidae family, for example, *Adelges laricis*;

(b) pest belonging to the Aleyrodidae family, for example, *Bemisia argentifolii*, *Bemisia tabaci* of *Bemisia* spp.; others such as *Aleurocanthus spiniferus*, *Dialeurodes citri*, *Trialeurodes vaporariorum*;

(c) pest belonging to the Aphididae family, for example, *Aphis craccivora*, *Aphis fabae*, *Aphis forbesi*, *Aphis gossypii*, *Aphis pomi*, *Aphis sambuci* and *Aphis spiraecola* of *Aphis* spp.; for example, *Rhopalosiphum maidis* and *Rhopalosiphum padi* of *Rhopalosiphum* spp.; for example, *Dysaphis plantaginea* and *Dysaphis radicola* of *Dysaphis* spp.; for example, *Macrosiphum avenae* and *Macrosiphum euphorbiae* of *Macrosiphum* spp.; for example, *Myzus cerasi*, *Myzus persicae* and *Myzus varians* of *Myzus* spp.; others such as *Acyrthosiphon pisum*, *Aulacorthum solani*, *Brachycaudus helichrysi*, *Brevicoryne brassicae*, *Chaetosiphon fragaefolii*, *Hyalopterus pruni*, *Hyperomyzus lactucae*, *Lipaphis erysimi*, *Megoura viciae*, *Metopolophium dirhodum*, *Nasonovia ribis-nigri*, *Phorodon humuli*, *Schizaphis graminum*, *Sitobion avenae*, *Toxoptera aurantii*;

(d) pest belonging to the Coccidae family, for example, *Ceroplastes ceriferus* and *Ceroplastes rubens* of *Ceroplastes* spp.;

(e) pest belonging to the Diaspididae family, for example, *Pseudaulacaspis pentagona* and *Pseudaulacaspis prunicola* of *Pseudaulacaspis* spp.; for example, *Unaspis euonymi* and *Unaspis yanonensis* of *Unaspis* spp.; others such as *Aonidiella aurantii*, *Comstockaspis perniciosa*, *Fiorinia theae*, *Pseudaonidia paeoniae*;

(f) pest belonging to the Margarodidae family, for example, *Drosicha corpulenta* and *Icerya purchasi*;

(g) pest belonging to the Phylloxeridae family, for example, *Viteus vitifolii*;

(h) pest belonging to the Pseudococcidae family, for example, *Planococcus citri* and *Planococcus kuraunhiae* of *Planococcus* spp.; others such as *Phenacoccus solani, Pseudococcus comstocki*;

(i) pest belonging to the Psyllidae family, for example, *Psylla mali* and *sylla pyrisuga* of *Psylla* spp.; others such as *Diaphorina citri*.

(4) Pest of Polyphaga Suborder (a) pest belonging to the Anobiidae family, for example, *Lasioderma serricorne*;

(b) pest belonging to the Attelabidae family, for example, *Byctiscus betulae, Rhynchites heros*;

(c) pest belonging to the Bostrichidae family, for example, *Lyctus brunneus*;

(d) pest belonging to the Brentidae family, for example, *Cylas formicarius*;

(e) pest belonging to the Buprestidae family, for example, *Agrilus sinuatus*;

(f) pest belonging to the Cerambycidae family, for example, *Anoplophora malasiaca, Monochamus alternatus, Psacothea hilaris, Xylotrechus pyrrhoderus*;

(g) pest belonging to the Chrysomelidae family, for example, *Bruchus pisorum* and *Bruchus rufimanus* of *Bruchus* spp.; for example, *Diabrotica barberi, Diabrotica undecimpunctata* and *Diabrotica virgifera* of *Diabrotica* spp.; for example, *Phyllotreta nemorum* and *Phyllotreta striolata* of *Phyllotreta* spp.; others such as *Aulacophora femoralis, Callosobruchus chinensis, Cassida nebulosa, Chaetocnema concinna, Leptinotarsa decemlineata, Oulema oryzae, Psylliodes angusticollis*;

(h) pest belonging to the Coccinellidae family, for example, *Epilachna varivestis* and *Epilachna vigintioctopunctata* of *Epilachna* spp.;

(i) pest belonging to the Curculionidae family, for example, *Anthonomus grandis* and *Anthonomus pomorum* of *Anthonomus* spp.; for example, *Sitophilus granaries* and *Sitophilus zeamais* of *Sitophilus* spp.; others such as *Echinocnemus squameus, Euscepes postfasciatus, Hylobius abietis, Hypera postica, Lissohoptrus oryzophilus, Otiorhynchus sulcatus, Sitona lineatus, Sphenophorus venatus*;

(j) pest belonging to the Elateridae family, for example, *Melanotus fortnumi* and *Melanotus tamsuyensis* of *Melanotus* spp.;

(k) pest belonging to the Nitidulidae family, for example, *Epuraea domina*;

(l) pest belonging to the Scarabaeidae family, for example, *Anomala cuprea* and *Anomala rufocuprea* of *Anomala* spp.; others such as *Cetonia aurata, Gametis jucunda, Heptophylla picea, Melolontha melolontha, Popillia japonica*;

(m) pest belonging to the Scolytidae family, for example, *Ips typographus*;

(n) pest belonging to the Staphylinidae family, for example, *Paederus fuscipes*;

(o) pest belonging to the Tenebrionidae family, for example, *Tenebrio molitor, Tribolium castaneum*;

(p) pest belonging to the Trogossitidae family, for example, *Tenebroides mauritanicus*.

(5) Pest of Diptera Order (A) Brachycera Suborder (a) pest belonging to the Agromyzidae family, for example, *Liriomyza bryoniae, Liriomyza chinensis, Liriomyza sativae* and *Liriomyza trifolii* of *Liriomyza* spp.; others such as *Chromatomyia horticola, Agromyza oryzae*;

(b) pest belonging to the Anthomyiidae family, for example, *Delia platura, Delia radicum* of *Delia* spp.; others such as *Pegomya cunicularia*;

(c) pest belonging to the Drosophilidae family, for example, *Drosophila melanogaster* and *Drosophila suzukii* of *Drosophila* spp.;

(d) pest belonging to the Ephydridae family, for example, *Hydrellia griseola*;

(e) pest belonging to the Psilidae family, for example, *Psila rosae*;

(f) pest belonging to the Tephritidae family, for example, *Bactrocera cucurbitae* and *Bactrocera dorsalis* of *Bactrocera* spp.; for example, *Rhagoletis cerasi* and *Rhagoletis pomonella* of *Rhagoletis* spp.; others such as *Ceratitis capitata, Dacus oleae*.

(B) Nematocera Suborder (a) pest belonging to the Cecidomyiidae family, for example, *Asphondylia yushimai, Contarinia sorghicola, Mayetiola destructor, Sitodiplosis mosellana*.

(6) Pest of Orthoptera Order (a) pest belonging to the Acrididae family, for example, *Schistocerca Americana* and *Schistocerca gregaria* of *Schistocerca* spp.; others such as *Chortoicetes terminifera, Dociostaurus maroccanus, Locusta migratoria, Locustana pardalina, Nomadacris septemfasciata, Oxya yezoensis*;

(b) pest belonging to the Gryllidae family, for example, *Acheta domestica, Teleogryllus emma*;

(c) pest belonging to the Gryllotalpidae family, for example, *Gryllotalpa orientalis*;

(d) pest belonging to the Tettigoniidae family, for example, *Tachycines asynamorus*.

(7) Acari (A) Acaridida of Astigmata Order:

(a) acari belonging to the Acaridae family, for example, *Rhizoglyphus echinopus* and *Rhizoglyphus robini* of *Rhizoglyphus* spp.; *Tyrophagus neiswanderi, Tyrophagus perniciosus, Tyrophagus putrescentiae* and *Tyrophagus similis* of *Tyrophagus* spp.; and others such as *Acarus siro, Aleuroglyphus ovatus, Mycetoglyphus fungivorus*;

(B) Actinedida of Prostigmata Order (a) acari belonging to the Tetranychidae family, for example, *Bryobia praetiosa* and *Bryobia rubrioculus* of *Bryobia* spp.; for example, *Eotetranychus asiaticus, Eotetranychus boreus, Eotetranychus celtis, Eotetranychus geniculatus, Eotetranychus kankitus, Eotetranychus pruni, Eotetranychus shii, Eotetranychus smithi, Eotetranychus suginamensis* and *Eotetranychus uncatus* of *Eotetranychus* spp.; for example, *Oligonychus hondoensis, Oligonychus ilicis, Oligonychus karamatus, Oligonychus mangiferus, Oligonychus orthius, Oligonychus perseae, ligonychus pustulosus, Oligonychus shinkajii* and *Oligonychus ununguis* of *Oligonychus* spp.; for example, *Panonychus citri, Panonychus mori* and *Panonychus ulmi* of *Panonychus* spp.; for example, *Tetranychus cinnabarinus, Tetranychus kanzawai, Tetranychus ludeni, Tetranychus quercivorus, Tetranychus phaselus, Tetranychus urticae* and *Tetranychus viennensis* of *Tetranychus* spp.; for example, *Aponychus corpuzae* and *Aponychus firmianae* of *Aponychus* spp.; for example, *Sasanychus akitanus* and *Sasanychus pusillus* of *Sasanychus* spp.; for example, *Shizotetranychus celarius, Shizotetranychus longus, Shizotetranychus miscanthi, Shizotetranychus recki* and *Shizotetranychus schizopus* of *Shizotetranychus* spp.; others such as *Tetranychina harti, Tuckerella pavoniformis, Yezonychus sapporensis*;

(b) acari belonging to the Tenuipalpidae family, for example, *Brevipalpus lewisi, Brevipalpus obovatus, Brevipalpus phoenicis, Brevipalpus russulus* and *Brevipalpus californicus* of *Brevipalpus* spp.; for example, *Tenuipalpus pacificus* and *Tenuipalpus zhizhilashviliae* of *Tenuipalpus* spp.; and others such as *Dolichotetranychus floridanus*;

(c) acari belonging to the Eriophyidae family, for example, *Aceria diospyri, Aceria ficus, Aceria japonica, Aceria kuko, Aceria paradianthi, Aceria tiyingi, Aceria tulipae* and *Aceria zoysiea* of *Aceria* spp.; for example, *Eriophyes chibaensis* and *Eriophyes emarginatae* of *Eriophyes* spp.; for example, *Aculops lycopersici* and *Aculops pelekassi* of *Aculops* spp.; for example, *Aculus fockeui, Aculus schlechtendali*, which belong *Aculus* spp.; and others such as *Acaphylla theavagrans, Calacarus carinatus, Colomerus vitis, Calepitrimerus vitis*, Epitrimerus pyri, Paraphytoptus kikus, Paracalacarus podocarpi, Phyllocotruta citri;

(d) acari belonging to the Transonemidae family, for example, *Tarsonemus bilobatus* and *Tarsonemus waitei* of *Tarsonemus* spp.; others such as *Phytonemus pallidus, Polyphagotarsonemus latus;*

(e) acari belonging to the Penthaleidae family, for example, *Penthaleus erythrocephalus* and *Penthaleus major* of *Penthaleus* spp.;

The harmful organism control agent of the present invention may be mixed with or used in combination with other active ingredients such as bactericides, insecticidal and acaricidal agents, nematicides, soil pesticides and the like; plant regulators, synergists, fertilizers, soil conditioners, animal feed or the like.

A combination of the compound of the present invention and another active ingredient can be expected to have a synergistic effect on insecticidal and acaricidal activity. The synergistic effect can be confirmed by the Colby's equation (Colby S. R.; Calculating Synergistic and Antagonistic Responses of Herbicide Combinations; Weeds 15, 20-22, 1967) according to a conventional method.

Examples of the insecticides/acaricides, nematocides, soil pesticides, anthelmintic agents and the like are as follow.

(1) Acetylcholine esterase inhibitor:

(a) Carbamate-based: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylycarb; fenothiocarb, MIPC, MPMC, MTMC, aldoxycarb, aliyxycarb, aminocarb, bufencarb, cloethocarb, metam-sodium, promecarb;

(b) Organic phosphorus-based: acephate, azamethiphos, azinphos-ethyl, azinphos-methyl, cadusafos, chlorethoxyfos, chlorfenvinphos, chlormephos, chlorpyriphos, chlorpyriphos-methyl, coumaphos, cyanophos, demeton-S-methyl, diazinon, dichlorvos/DDVP, dicrotophos, dimethoate, dimethylvinfos, disulfoton, EPN, ethion, ethoprophos, famphur, fenamiphos, fenitrothion, fenthion, fosthiazete, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridafenthion, quinalphos, sulfotep, tebupirimfos, temephos, terbufos, tetrachlorvinphos, thiometon, triazophos, trichlorfon, vamidothion; bromophos-ethyl, BRP, carbophenothion, cyanofenphos, CYAP, demeton-S-methyl sulphone, dialifos, dichlofenthion, dioxabenzofos, etrimfos, fensulfothion, flupyrazofos, fonofos, formothion, fosmethilan, isazophos, iodofenphos, methacrifos, pirimiphos-ethyl, phosphocarb, propaphos, prothoate, sulprofos.

(2) GABA-agonistic chloride ion channel antagonist: acetoprole, chlordane, endosulfan, ethiprole, fipronil, pyraflupole, pyriprole; camphechlore, heptachlor, dienochlor.

(3) Sodium channel modulator: acrinathrin, d-cis-trans-allethrin, d-trans allethrin, bifenthrin, bioallethrin, bioallethrin S-cyclopentyl isomer, bioresmethrin, cycloprotophosphorus, cycloprothrin, cyfluthrin, β-cyfluthrin, cyhalothrin, λ-cyhalothrin, γ-cyhalothrin, cypermethrin, α-cypermethrin, β-cypermethrin, θ-cypermethrin, ξ-cypermethrin, cyphenothrin [(1R)-trans isomer], δ-methrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrum, resmethrin, silafluofen, tefluthrin, tetramethrin, tetramethrin [(1R)-isomer], tralomethrin, transfluthrin; allethrin, pyrethrin, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, terallethrin.

(4) Nicotinic acetylcholine receptor agonist: acetamiprid, clothianidin, dinotefuran, imidacloprid, nitenpyram, nithiazine, thiacloprid, thiamethoxam, sulfoxaflor, nicotine, flupyradifurone.

(5) Nicotinic acetylcholine receptor allosteric modulator: spinetoram, spinosad.

(6) Chloride channel activator: abamectin, emamectinebenzoate, lepimectin, milbemectin; ivermectin, seramectin, doramectin, eprinomectin, moxidectin; milbemycin; milbemycin oxime.

(7) Juvenile hormone-like substances: hydroprene, kinoprene, methoprene, fenoxycarb, pyriproxyfen, diofenolan, epofeneonane, triprene.

(8) Other nonspecific inhibitor: methyl bromide, chloropicrin, sulfuryl fluoride, borax, tartar emetic.

(9) Homoptera selective feeding inhibitor: flonicamid, pymetrozine, pyrifluquinazon.

(10) Acari growth inhibitor: clofentezine, diflovidazin, hexythiazox, etoxazole.

(11) Microorganism-derived insect midgut inner membrane distrupting agent: *Bacillus thuringiensis* subsp. *Israelensi, Bacillus sphaericus, Bacillus thuringiensis* subsp. *Aizawai, Bacillus thuringiensis* subsp. *Kurstaki, Bacillus thuringiensis* subsp. *Tenebrionis*, Bt crop protein: Cry1Ab, Cry1Ac, Cry1Fa, Cry1A.105, Cry2Ab, Vip3A, mCry3A, Cry3Ab, Cry3Bb, Cry34Ab 1/Cry35Ab 1.

(12) Mitochondria ATP biosynthesis enzyme inhibitor: diafenthiuron, azocyclotin, cyhexitin, fenbutatin oxide, propargite, tetradifon.

(13) Oxidative phosphorylation uncoupling agent: chlorfenapyr, sulfluramid, DNOC; binapacryl, dinobuton, dinocap.

(14) Nicotinic acetylcholine receptor channel blocker: bensultap, cartap hydrochloride; nereistozin; thiosultap-sodium, thiocyclam.

(15) Chitin synthesis inhibitor: bistrifluron, chlorfluazuron, diflubenzuron, flucycloxuron, flufenoxuron, hexaflumuron, lufenuron, novaluron, nobifumuron, teflubenzuron, triflumuron, buprofezin, fluazuron.

(16) Diptera molting disturbing agent: cyromazine.

(17) Molting hormone receptor agonist: chromafenozide, halofenozide, methoxyfenozide, tebufenozide.

(18) Octopamine receptor agonist: amitraz, demiditraz, chlordimeform.

(19) Mitochondria electron transfer chain complex III inhibitor: acequinocyl, fluacrypyrim, hydramethylnon.

(20) Mitochondria electron transfer chain complex I inhibitor: fenazaquin, fenproximate, pyrimidifen, pyridaben, tebufenpyrad, tolfenpyrad, rotenone.

(21) Voltage-dependent sodium channel blocker: indoxacarb, metaflumizone.

(22) Acetyl CoA carboxylase inhibitor: spirodiclofen, spiromesifen, spirotetramat.

(23) Mitochondria electron transfer chain complex IV inhibitor: aluminium phosphide, calcium phosphide, phosphine, zinc phosphide, cyanide.

(24) Mitochondria electron transfer chain complex II inhibitor: cyenopyrafen, cyflumetofen, pyflubumide.

(25) Ryanodine receptor modulator: chlorantraniliprole, cyantraniliprole, flubendiamide, cyclaniliprole, tetraniliprole.

(26) Mixed function oxidase inhibitor compound: piperonyl butoxide.

(27) Latrophilin receptor agonist: depsipeptide, cyclodepsipeptide, 24 membered cyclodepsipeptide, emodepside.

(28) Others (action mechanism is unknown): azadirachtin, benzoximate, bifenazate, bromopropylate, quinomethionate, cryolite, dicofol, pyridalyl; benclothiaz, sulfur, amidoflumet, 1, 3-dichloropropene, DCIP, phenisobromolate, benzomate, methaldehyde, chlorobenzilate, chlothiazoben, dicyclanil, fenoxacrim, fentrifanil, flubenzimine, fluphenazine, gossyplure, japonilure, metoxadiazone, oil, potassium oleate, tetrasul; triarathene; afidopyropen, flometoquin, flufiprole, fluensulfone, meperfluthrin, tetramethylfluthrin, tralopyril, dimefluthrin, methylneodecanamide; fluralaner, afoxolaner, fluxametamide, 5-[5-(3,5-dichlorophenyl)-5-trifluoromethyl-4,5-dihydroisoxazole-3-yl]-2-(1H-1,2,4-triazole-1-yl)benzonitrile (CAS:943137-49-3), broflanilide, other metadiamide type.

(29) Antiparastic agent:
(a) benzimidazoles: fenbendazole, albendazole, triclabendazole, oxibendazole, mebendazole, oxfendazole, parbendazole, flubendazole; febantel, netobimin, thiophanate; thiabendazole, cambendazole;
(b) salicylanilides: closantel, oxyclozanide, rafoxanide, niclosamide;
(c) substituted phenols: nitroxinil, nitroscanate;
(d) pyridines: pyrantel, morantel;
(e) imidazothiazoles: levamisole, tetramisole;
(f) tetrahydropyrimidines: praziquantel, epsiprantel;
(g) other antiparastic agents: cyclodiene, riania, clorsulon, metronidazole, demiditraz; piperazine, diethyl carbamazine, dichlorophen, monepantel, tribendimidine, amidantel; thiacetarsamide, melorsamine, arsenamide.

Specific examples of the bactericide which can be mixed with or used in combination with the harmful organism control agent of the present invention are shown below.

(1) Nucleic acid biosynthesis inhibitor:
(a) RNA polymerase I inhibitor: benalaxyl, benalaxyl-M, furalaxyl, metalaxyl, metalaxyl-M, oxadixyl; clozylacon, ofurace;
(b) adenosine deaminase inhibitor: bupirimate, dimethirimol, ethirimol;
(c) DNA/RNA synthesis inhibitor: hymexazol, octhilinone;
(d) DNA topoisomerase II inhibitor: oxolinic acid;
(2) karyokinesis inhibitor and cell division inhibitor:
(a) β-tubulin polymerization inhibitor: benomyl, carbendazim, chlorfenazole, fuberidazole, thiabendazole; thiophanate, thiophanate-methyl; diethofencarb; zoxamide; ethaboxam;
(b) cell division inhibitor: pencycuron;
(c) delocalization inhibitor of spectrin-like protein: fluopicolide;
(3) Respiration inhibitor:
(a) complex I NADH oxidation-reduction inhibitor: diflumetorim; tolfenpyrad;
(b) complex II succinic acid dehydrogenase inhibitor: benodanil, flutolanil, mepronil; isofetamid, fluopyram; fenfuram, furmecyclox; carboxin, oxycarboxin; thifluzamide; benzovindiflupyr, bixafen, fluxapyroxad, furametpyr, isopyrazam, penflufen, penthiopyrad, Sedaxan; boscalid;
(c) complex III ubiquinol oxidase Qo inhibitor: azoxystrobin, coumoxystrobin, coumethoxystrobin, enoxastrobin, flufenoxystrobin, picoxystrobin, pyraoxystrobin; pyraclostrobin, pyrametostrobin, triclopyricarb; kresoxim-methyl, trifloxystrobin; dimoxystrobin, fenaminstrobin, metominostrobin, orysastrobin; famoxadone; fluoxastrobin; fenamidone; pyribencarb;
(d) complex III ubiquinol reductase Qi inhibitor: cyazofamid; amisulbrom;
(e) oxidative phosphorylation uncoupling agent: binapacryl, meptyldinocap, dinocap; fluazinam; ferimzone;
(f) oxidative phosphorylation inhibitor (ATP synthase inhibitor): fenthin acetate, fentin chloride, fentin hydroxide;
(g) ATP production inhibitor: silthiofam;
(h) complex III cytochrome bc1 (ubiquinone reductase) Qx (unknown) inhibitor: ametoctradin;
(4) Amino acid and protein synthesis inhibitor
(a) methionine biosynthesis inhibitor: andoprim, cyprodinil, mepanipyrim, pyrimethanil;
(b) protein synthesis inhibitor: blasticidin-S; kasugamycin; kasugamycin hydrochloride; streptomycin; oxytetracycline.
(5) Signal transfer inhibitor:
(a) quinoxyfen, proquinazid;
(b) MAP/histidine kinase inhibitor in osmotic pressure signal transfer: fenpiconil, fludioxonil; chlozolinate, iprodione, procymidone, vinclozolin;
(6) Lipid and cell membrane synthesis inhibitor:
(a) phospholipid biosynthesis and methyltransferase inhibitor: edifenphos, iprobenfos, pyrazophos; isoprothiolane;
(b) lipid peroxide agent: biphenyl, chloroneb, dichloran, quintozene, tecnazene, tolclofos-methyl; etridiazole;
(c) agents affecting cell membrane: iodocarb, propamocarb, propamocarb hydrochloride, propamocarb-fosetylate, prothiocarb;
(d) microorganisms disturbing virus cell membrane: *Bacillus subtilis, Bacillus subtilis* strain QST713, *Bacillus subtilis* strain FZB24, *Bacillus subtilis* strain MBI600, *Bacillus subtilis* strain D747;
(e) agents disturbing cell membrane: *melaleuca alternifolia* (tea tree) extract.
(7) Cell membrane sterol biosynthesis inhibitor:
(a) C14 position demethylation inhibitor in sterol biosynthesis: triforine; pyrifenox, pyrisoxazole; fenarimol, flurprimidol, nuarimol; imazalil, imazalil-sulphate, oxpoconazole, pefurazoate, prochloraz, triflumizole, viniconazole; azaconazole, bitertanol, bromconazole, cyproconazole, diclobutrazol, difenoconazole, diniconazole, diniconazole-M, epoxyconazole, etaconazole, fenbuconazole, fluquinconazole, flusilazole, flutriafol, furconazole, furconazole-cis, hexaconazole, imibenconazole, ipuconazole, metconazole, myclobutanil, penconazole, propiconazole, quinconazole, simeconazole, tebuconazole, tetraconazole, triadimefon, triadimenol, triticonazole; prothioconazole, voriconazole;
(b) Δ14 reductase and Δ8→Δ7-isomerase inhibitor in sterol biosynthesis: aldimorph, dodemorph, dodemorph-acetate, fenpropimorph, tridemorph, fenpropidine, piperalin; spiroxamine;

(c) 3-keto reductase inhibitor in C4 position demethylation in sterol biosynthesis system: fenhexamid; fenpyrazamine;
(d) squalene epoxidase inhibitor in sterol biosynthesis system: pyributicarb; naftifen, terbinafine.
(8) cell wall synthesis inhibitor
(a) trehalase inhibitor: validamycin;
(b) chitin synthetase inhibitor: polyoxins, polyoxorim;
(c) cellulose synthetase inhibitor: dimethomorph, flumorph, pyrimorph; benthiavalicarb, iprovalicarb, tolprocarb, valifenalate; mandipropamide;
(9) Melanin biosynthesis inhibitor
(a) reductase inhibitor in melamin biosynthesis: fthalide; pyroquilon; tricyclazole;
(b) anhydrase inhibitor in melanin biosynthesis: carpropamid; diclocymet; fenoxanil;
(10) Resistance-inducing agent of host plant:
(a) agents affecting salicylic acid synthetic pathway: acibenzolar-s-methyl;
(b) others: probenazole; tiadinil; isotianil; laminarin; *Reynoutria sachalinensis* extract.
(11) agents of which the activity is unknown: cymoxanil, fosetyl-aluminium, phosphoric acid (phosphate), tecloftalam, triazoxide, flusulfamide, diclomezine, methasulfocarb, cyflufenamid, metrafenone, pyriofenone, dodine, dodine free base, flutianil.
(12) Agent having multy activities: copper (copper salt), bordeaux mixture, copper hydroxide, copper naphthalate, copper oxide, oxychloride copper, copper sulfate, sulfur, sulfur product, calcium polysulfide; ferbam, mancozeb, maneb, mancopper, metiram, polycarbamate, propineb, thiram, zineb, ziram; captan, captafol, folpet; chlorothalonil; dichlofluanid, tolylfluanid; guazatine, iminoctadine triacetate, iminoctadine trialbesilate; anilazine; dithianon; quinomethionate; fluoroimide.
(13) Other agents: DBEDC, fluorofolpet, guazatine acetate, bis(8-quinolinolato) copper (II), propamidine, chloropicrin, cyprofuram, agrobacterium, bethoxazin, diphenylamine, methyl isothiocyanate (MITC), mildew-mycin, capsaicin, curfraneb, cyprosulfamide, dazomet, debacarb, dichlorophen, difenzoquat, difenzoquat.methyl sulfonate, flumetover, fosetyl.calcium, fosetyl.sodium, irmamycin, natamycin, nitrothal isopropyl, oxamocarb, puropamocin sodium, pyrrolnitrin, tebufloquin, tolnifanide, zarilamide, algophase, amicarthiazol, oxathiapiprolin, metiram zinc, benthiazole, trichlaamide, uniconazole, mildew-mycin, oxyfenthiin, picarbutrazox.

Specific examples of the plant growth regulators which can be mixed with or used in combination with the harmful organism control agent of the present invention are shown below.

abscisic acid, kinetin, benzylaminopurine, 1,3-diphenylurea, forchlorfenuron, thidiazuron, chlorfenuron, dihydrozeatin, gibberelline A, gibberelline A4, gibberelline A7, gibberelline A3, 1-methylcyclopropene, N-acetyl aminoethoxyvinyl glycine (aviglycine), aminooxyacetate, silver nitrate, cobalt chloride, IAA, 4-CPA, cloprop, 2,4-D, MCPB, indole-3-butyrate, dichlorprop, phenothiol, 1-naphthyl acetamide, ethychlozate, cloxyfonac, maleic acid hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenyl ethyl)aminobutyric acid; ethephon, chlormequat, mepiquat chloride, benzyl adenine, 5-amino levulinic acid.

[External Parasite Control Agent]

The external parasite control agent of the present invention includes at least one of the diarylazole compound of the present invention as an active ingredient. The diarylazole compound of the present invention has superior effect for preventing the external parasites that are harmful to humans and animals.

Examples of the external parasite include acari, louse, flea, mosquito, biting housefly, flesh fly and the like.

Examples of the host animals to be treated by the external parasite control agent of the present invention include warm-blooded animals such as pet animals for example, dogs, cats or the like; pet birds; domestic animals for example, cows, horses, pigs, sheep or the like; domestic fowl; and the like. In addition, honeybees, stag beetles may also be exemplified.

The external parasites live on the host animals, especially live inside or upon the warm-blooded animals. More specifically, the external parasites are parasitic in the back, armpit, underbelly, inner thigh and the like of the host animals and obtain nutritional sources such as blood, dandruff from the animals to live.

The external parasite control agent of the present invention can be applied by a known veterinary method (topical, oral, parenteral or subcutaneous administration). Examples of the method include orally administering tablets, capsules and foods mixed with the external parasite control agent to the animals; administering to the animals by using immersion liquid, suppository or injection (intramuscular, subcutaneous, intravenous, intraabdominal or the like); topically administering oily or aqueous liquid preparation by spraying, pouring on, spotting on or the like; topically administering by attaching a collar, ear tag or the like made by molding a mixture obtained by kneading the external parasite control agent with a resin to the animals; and the like.

Specific examples of the external parasite able to be prevented are as follows.

(1) Acari

Acari belonging to the Dermanyssidae family, acari belonging to the Macronyssidae family, acari belonging to the Laelapidae family, acari belonging to the Varroidae family, acari belonging to the Argasidae family, acari belonging to the Ixodidae family, acari belonging to the Psoroptidae family, acari belonging to the Sarcoptidae family, acari belonging to the Knemidokoptidae family, acari belonging to the Demodixidae family, acari belonging to the Trombiculidae family, insect-parasitic acari such as Coleopterophagus berlesei or the like.

(2) Phthiraptera Order

Louse belonging to the Haematopinidae family, louse belonging to the Linognathidae family, biting louse belonging to the Menoponidae family, biting louse belonging to the Philopteridae family, biting louse belonging to the Trichodectidae family;

(3) Siphonaptera Order

Flea belonging to the Pulicidae family, for example, *Ctenocephalides canis* and *Ctenocephalides felis* of *Ctenocephalides* spp.;

Flea belonging to the Tungidae family, flea belonging to the Ceratophyllidae family, flea belonging to the Leptopsyllidae family;

(4) Hemiptera Order (5) Harmful Organism of Diptera Order

Mosquito belonging to the Culicidae family, black fly belonging to the Simuliidae family, punkie belonging to the Ceratopogonidae family, fly belonging to the Tabanidae family, fly belonging to the Muscidae family, *glossina* belonging to the Glossinidae family; flesh fly belonging to the Sarcophagidae family, fly belonging to the Hippoboscidae family, fly belonging to the Calliphoridae family, fly belonging to the Oestridae family;

[Internal Parasite Control or Extermination Agent]

The internal parasite control or extermination of the present invention include at least one selected from the diarylazole compound of the present invention as an active ingredient.

The parasites to be prevented by the internal parasite control or extermination agent of the present invention live in host animals, especially live inside of the worm-blooded animals or fishes (internal parasite). Examples of the host animals for which the internal parasite control or extermination agent of the present invention is applicable include worm-blooded animals such as humans, domestic mammals (for example, cows, horses, pigs, sheep, goats or the like), experimental animals (for example, mice, rats, merines unduiculatus or the like), pet animals (for example, hamsters, guinea pigs, dogs, cats, horses, squirrels, rabbits, ferrets or the like), wild animals and zoo mammals (for example, monkeys, foxes, deer, buffaloes or the like), domestic fowl (for example, turkeys, ducks, chickens, quail or the like), pet birds (for example, pigeon, parrot, magpie, java sparrow, parakeet, bengalee, canary or the like); fishes such as salmon, trout, Koi or the like; and the like. By preventing or exterminating the parasites, parasitic disease carried by parasites can be prevented or treated.

Examples of the parasites to be prevented or exterminated are as follows.

(1) Nematode of Enoplida Order (a) *Dioctophyma renale* belonging to the Dioctophymatidae family, for example, *Dioctophyma renale* of *Dioctophyma* spp.;

(b) *Dioctophyma renale* belonging to the Soboliphymatidae family, for example, *Soboliphyme abei* and *Soboliphyme baturini* of *Soboliphyme* spp.;

(2) Nematode of Trichocephalida Order (a) *Trichinella spiralis* belonging to the Trichinellidae family, for example, *Trichinella spiralis* of *Trichinella* spp.;

(b) whipworms belonging to the Trichuridae family, for example, *Capillaria annulata, Capillaria contorta, Capillaria hepatica, Capillaria perforans, Capillaria plica* and *Capillaria suis* of *Capillaria* spp.; *Trichuris vulpis, Trichuris discolor, Trichuris ovis, Trichuris skrjabini* and *Trichuris suis* of *Trichuris* spp.;

(3) Nematode of Rhabditida Order

*Strongyloides stercoralis* belonging to the Strongyloididae family, for example, *Strongyloides papillosus, Strongyloides planiceps, Strongyloides ransomi, Strongyloides suis, Strongyloides stercoralis, Strongyloides tumefaciens* and *Strongyloides ratti* of *Strongyloides* spp.;

(4) Nematode of Strongylida Order

Hookworm belonging to the Ancylostomatidae family, for example, *Ancylostoma braziliense, Ancylostoma caninum, Ancylostoma duodenale* and *Ancylostoma tubaeforme* of *Ancylostoma* spp.; *Uncinaria stenocephala* of *Uncinaria* spp.; *Bunostomum phlebotomum* and *Bunostomum trigonocephalum* of *Bunostomum* spp.;

(5) Nematode of Strongylida Order (a) Nematode belonging to the Angiostrongylidae family, for example, *Aelurostrongylus abstrusus* of *Aelurostrongylus* spp.; *Angiostrongylus vasorum* and *Angiostrongylus cantonesis* of *Angiostrongylus* spp.;

(b) Nematode belonging to the Crenosomatidae family, for example, *Crenosoma aerophila* and *Crenosoma vulpis* of *Crenosoma* spp.;

(c) Nematode belonging to the Filaroididae family, for example, *Filaroides hirthi* and *Filaroides osleri* of *Filaroides* spp.;

(d) Lung worms belonging to the Metastrongylidae family, for example, *Metastrongylus apri, Metastrongylus asymmetricus, Metastrongylus pudendotectus* and *Metastrongylus salmi* of *Metastrongylus* spp.;

(e) Gapeworms trachea belonging to the Syngamidae family, for example, *Cyathostoma bronchialis* of *Cyathostoma* spp.; *Syngamus skrjabinomorpha* and *Syngamus trachea* of *Syngamus* spp.;

(6) Nematode of Strongylida Order (a) Nematode belonging to the Molineidae family, for example, *Nematodirus filicollis* and *Nematodirus spathiger* of *Nematodirus* spp.;

(b) Nematode belonging to the Dictyocaulidae family, for example, *Dictyocaulus filarial* and *Dictyocaulus viviparous* of *Dictyocaulus* spp.;

(c) Nematode belonging to the Haemonchidae family, for example, *Haemonchus contortus* of *Haemonchus* spp.; *Mecistocirrus digitatus* of *Mecistocirrus* spp.;

(d) Nematode belonging to the Haemonchidae family, for example, *Ostertagia ostertagi* of *Ostertagia* spp.;

(e) Nematode belonging to the Heligmonellidae family, for example, *Nippostrongylus braziliensis* of *Nippostrongylus* spp.;

(f) Nematode belonging to the Trichostrongylidae family, for example, *Trichostrongylus axei, Trichostrongylus colubriformis* and *Trichostrongylus tenuis* of *Trichostrongylus* spp.; *Hyostrongylus rubidus* of *Hyostrongylus* spp.; *Obeliscoides cuniculi* of *Obeliscoides* spp.;

(7) Nematode of Strongylida Order (a) Nematode belonging to the Chabertiidae family, for example, *Chabertia ovina* of *Chabertia* spp.; *Oesophagostomum brevicaudatum* (pig), *Oesophagostomum columbianum, Oesophagostomum dentatum, Oesophagostomum georgianum* (pig), *Oesophagostomum maplestonei, Oesophagostomum quadrispinulatum* (pig), *Oesophagostomum radiatum, Oesophagostomum venulosum* and *Oesophagostomum watanabei* of *Oesophagostomum* spp.;

(b) Nematode belonging to the Stephanuridae family, for example, *Stephanurus dentatus* of *Stephanurus* spp.;

(c) Nematode belonging to the Strongylidae family, for example, *Strongylus asini, Strongylus edentates, Strongylus equinus* and *Strongylus vulgaris* of *Strongylus* spp.;

(8) Nematode of the Oxyurida Order

Nematode belonging to the Oxyuridae family, for example, *Enterobius anthropopitheci* and *Enterobius vermicularis* of *Enterobius* spp.; *Oxyuris equi* of *Oxyuris* spp.; *Passalurus ambiguous* of *Passalurus* spp.;

(9) Nematode of Ascaridida Order (a) Nematode belonging to the Ascaridiidae family, for example, *Ascaridia galli* of *Ascaridia* spp.;

(b) Nematode belonging to the Heterakidae family, for example, *Heterakis beramporia, Heterakis brevispiculum, Heterakis gallinarum, Heterakis pusilla* and *Heterakis putaustralis* of *Heterakis* spp.;

(c) Nematode belonging to the Anisakidae family, for example, *Anisakis simplex* of *Anisakis* spp.;

(d) Nematode belonging to the Ascarididae family, for example, *Ascaris lumbricoides* and *Ascaris suum* of *Ascaris* spp.; *Parascaris equorum* of *Parascaris* spp.;

(e) Nematode belonging to the Toxocaridae family, for example, *Toxocara canis, Toxocara leonine, Toxocarasuum, Toxocara vitulorum* and *Toxocara cati* of *Toxocara* spp.;

(10) Nematode of Spirurida Order (a) Nematode belonging to the Onchocercidae family, for example, *Brugia malayi, Brugia pahangi* and *Brugia patei* of *Brugia* spp.; *Dipetalonema reconditum* of *Dipetalonema* spp.; *Dirofilaria immitis* of *Dirofilaria* spp.; *Filaria oculi* of *Filaria* spp.; *Onchocerca* cervicalis, *Onchocerca gibsoni* and *Onchocerca gutturosa* of *Onchocerca* spp.;

(b) Nematode belonging to the Setariidae family, for example, *Setaria digitate, Setaria equine, Setaria labiatopapillosa* and *Setaria marshalli* of *Setaria* spp.; *Wuchereria bancrofti* of *Wuchereria* spp.;

(c) Nematode belonging to the Filariidae family, for example, *Parafilaria multipapillosa* of *Parafilaria* spp.; *Stephanofilaria assamensis, Stephanofilaria dedoesi, Stephanofilaria kaeli, Stephanofilaria okinawaensis* and *Stephanofilaria stilesi* of *Stephanofilaria* spp.;

(11) Nematode of Spirurida Order (a) Nematode belonging to the Gnathostomatidae family, for example, *Gnathostoma doloresi* and *Gnathostoma spinigerum* of *Gnathostoma* spp.;

(b) Nematode belonging to the Habronematidae family, for example, *Habronema majus, Habronema microstoma* and *Habronema muscae* of *Habronema* spp.; *Draschia megastoma* of *Draschia* spp.;

(c) Nematode belonging to the Physalopteridae family, for example, *Physaloptera canis, Physaloptera cesticillata, Physaloptera erdocyona, Physaloptera felidis, Physaloptera gemina, Physaloptera papilloradiata, Physaloptera praeputialis, Physaloptera pseudopraerutialis, Physaloptera rara, Physaloptera sibirica* and *Physaloptera vulpineus* of *Physaloptera* spp.;

(d) Nematode belonging to the Gongylonematidae family, for example, *Gongylonema pulchrum* of *Gongylonema* spp.;

(e) Nematode belonging to the Spirocercidae family, for example, *Ascarops strongylina* of *Ascarops* spp.;

(f) Nematode belonging to the Thelaziidae family, for example, *Thelazia callipaeda, Thelazia gulosa, Thelazia lacrymalis, Thelazia rhodesi* and *Thelazia skrjabini* of *Thelazia* spp.;

[Control Agents Against Other Harmful Organisms]

Other than the above described harmful organisms, the harmful organism control agent of the present invention also has a superior effect for preventing the pests having a stinger or venom to damage humans and animals, pests carrying various pathogens and pathogenic bacterias, and pests giving unpleasant feelings to humans (toxic pest, hygiene pest, unpleasant pest).

Specific examples are as follows.

(1) Pests of Hymenoptera Order

Bees belonging to the Argidae family, bees belonging to the Cynipidae family, bees belonging to the Diprionidae family, alis belonging to the Formicidae family, bees belonging to the Mutillidae vamily family, bees belonging to the Vespidae family.

(2) Other Pests

Blattodea, termite, Araneae, centipede, millipede, crustacea, *Cimex lectularius*.

[Preparation Formulation]

Several examples of the harmful organism control agent, insecticide or acaricide, external parasite control agent, or internal parasite control or extermination agent of the present invention are shown bellow. However, the additives and the addition ratios are not limited to the examples and can be modified over a wide range. The term "part" in the preparation formulation indicates "part by weight".

The followings are the preparation formulations for agricultural and horticultural use and for paddy rice.

(Preparation 1: Wettable Powder)

40 parts of the diarylazole compound of the present invention, 53 parts of diatom earth, 4 parts of fatty alcohol sulfate and 3 parts of alkylnaphthalene sulfonate were uniformly mixed and finely pulverized to obtain a wettable powder including 40% of active ingredient.

(Preparation 2: Emulsion)

30 parts of the diarylazole compound of the present invention, 33 parts of xylene, 30 parts of dimethylformamide and 7 parts of polyoxyethylene alkylaryl ether were mixed and dissolved to obtain an emulsion including 30% of active ingredient.

(Preparation 3: Granules)

5 parts of the diarylazole compound of the present invention, 40 parts of talc, 38 parts of clay, 10 parts of bentonite and 7 parts of sodium alkylsulfate were uniformly mixed and crushed, followed by granulating into a granular shape having a diameter of 0.5 to 1.0 mm to obtain granules containing 5% active ingredient.

(Preparation 4: Granules)

5 parts of the diarylazole compound of the present invention, 73 parts of clay, 20 parts of bentonite, 1 part of sodium dioctyl sulfosuccinate and 1 part of potassium phosphate were thoroughly crushed and mixed followed by the addition of water, mixing well, granulating and drying to obtain granules containing 5% active ingredient.

(Preparation 5: Suspension)

10 parts of the diarylazole compound according to the present invention, 4 parts of polyoxyethylene alkyl allyl ether, 2 parts of sodium polycarboxylate, 10 parts of glycerin, 0.2 parts of xanthan gum and 73.8 parts of water were mixed and wet-crushed to a grain size of 3 microns or less to obtain a suspension containing 10% active ingredient.

The following are the preparation formulations of the external parasite control agent, or internal parasite control or extermination agent.

(Preparation 6: Granulated Powder)

5 part of the diarylazole compound of the present invention was dissolved in an organic solvent to obtain a solution, and sprayed the solution on 94 parts of kaolin and 1 part of white carbon, followed by evaporating the solvent under reduced pressure. This kind of granulated powder may be mixed with animal food.

(Preparation 7: Impregnating Agent)

0.1-1 parts of the diarylazole compound of the present invention and 99-99.9 parts of peanut oil were uniformly mixed, and then filter-sterilized by a sterilizing filter after adjustment.

(Preparation 8: Pour-on Agent)

5 parts of the diarylazole compound of the present invention, 10 parts of myristic acid ester and 85 parts of isopropanol were uniformly mixed to obtain a pour-on agent.

(Preparation 9: Spot-on Agent)

10-15 parts of the diarylazole compound of the present invention, 10 parts of palmitic acid ester and 75-80 parts of isopropanol were uniformly mixed to obtain a spot-on agent.

(Preparation 10: Spray-on Agent)

1 part of the diarylazole compound of the present invention, 10 parts of propylene glycol and 89 parts of isopropanol were uniformly mixed to obtain a spray-on agent.

The following provides compound Examples to explain the present invention more specifically. However, the present invention is not limited to the following compound examples.

Example 1

Synthesis of 1-(2-(ethylsulfonyl)-4-(trifluoromethyl)phenyl)-4-(4-(trifluoromethoxy)phenyl)-1H-pyrazol-5-amine (Compound No. 1-12) and 5-chloro-1-(2-(ethylsulfonyl)-4-(trifluoromethyl)phenyl)-4-(4-(trifluoromethoxy)phenyl)-1H-pyrazole (Compound No. 1-17)

Step 1-1

Synthesis of 2-ethylthio-1-fluoro-4-(trifluoromethyl)benzene

[Chemical formula 11]

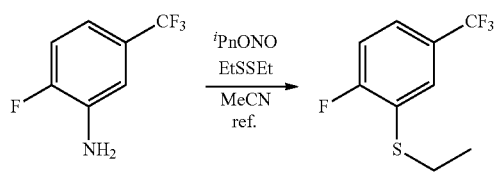

22 g (0.12 mol) of 2-fluoro-5-(trifluoromethyl) aniline and 7.3 g (0.060 mol, 0.5 eq) of diethyl disulfide were dissolved in 300 ml of acetonitrile and heated to 30° C. Then, 14 g (0.12 mol, 1.0 eq) of isopentyl nitrite was added dropwise thereto, and the obtained mixture was stirred under heating reflux for 1 hour. The reaction solution was concentrated under reduced pressure, and the obtained residue was purified by silica gel column chromatography to obtain 11 g (yield 39%) of the target product.

$^1$H-NMR of the obtained target product is shown below.
$^1$H-NMR (400 MHz, CDCl$_3$): δ 7.59 (m, 1H), 7.46 (m, 1H), 7.15 (m, 1H), 2.98 (q, 2H), 1.33 (t, 3H).

Step 1-2

Synthesis of 2-(ethylsulfonyl)-1-fluoro-4-(trifluoromethyl)benzene

[Chemical formula 12]

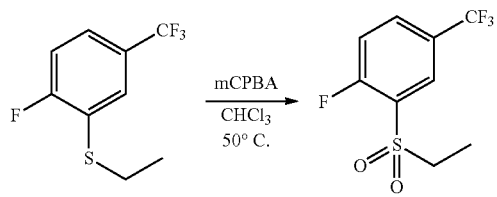

1.9 g (8.5 mmol) of 2-ethylthiol-fluoro-4-(trifluoromethyl) benzene was dissolved in 80 ml of chloroform and stirred at room temperature. Then, 5.2 g (70%, 21 mmol; 2.5 eq) of metachloroperbenzoic acid was added thereto and the obtained mixture was stirred at 50° C. overnight. The resulting reaction solution was poured into a mixed solution of a saturated sodium hydrogen carbonate aqueous solution and a saturated sodium thiosulfate aqueous solution, and then extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 2.0 g (yield: 80%) of the target product.

$^1$H-NMR of the obtained target product is shown below.
$^1$H-NMR (400 MHz, CDCl$_3$): δ 8.26 (m, 1H), 7.94 (m, 1H), 7.40 (m, 1H), 3.37 (q, 2H), 1.35 (t, 3H).

Step 1-3

Synthesis of ethyl 5-amino-1-(2-(ethyl sulfonyl)-4-(trifluoromethyl)phenyl)-1H-pyrazole-4-carboxylate

[Chemical formula 13]

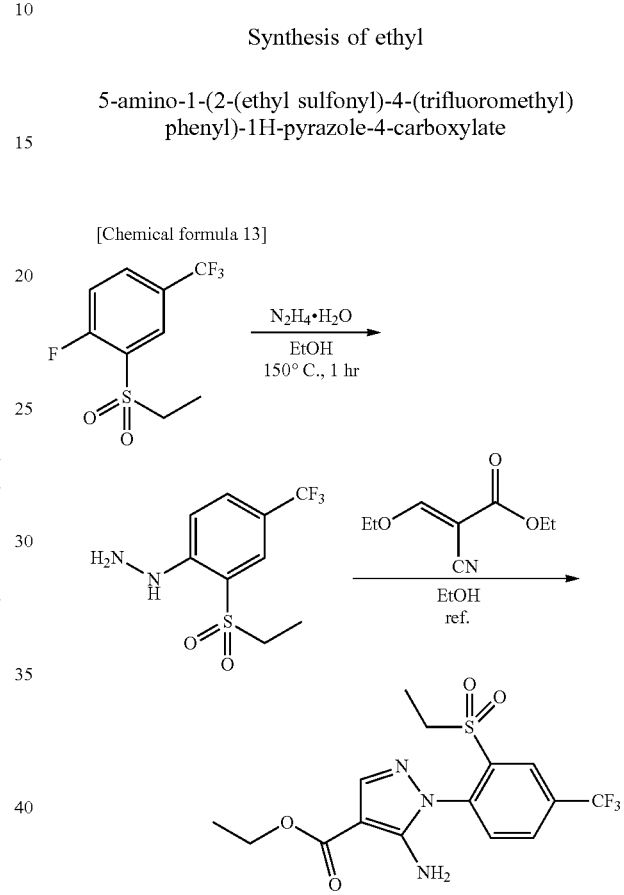

2.0 g (7.6 mmol) of 2-(ethylsulfonyl)-1-fluoro-4-(trifluoromethyl)benzene was dissolved in 15 ml of ethanol and stirred at room temperature. Then, 3.0 g (61 mmol, 8.0 eq) of hydrazine monohydrate was added thereto, and the resulting mixture was reacted at 150° C. for 1 hour. The reaction solution was poured into water and extracted with toluene. The obtained organic layer was washed with saturated brine, dried over anhydrous magnesium sulfate, and filtered. The filtrate was concentrated under reduced pressure, the obtained residue was dissolved in 13 ml of ethanol, and the mixture was stirred at room temperature. Then, 1.3 g (7.6 mmol, 1.0 eq) of ethyl(ethoxymethylene)cyanoacetate was added thereto, and the resulting mixture was stirred under heating reflux overnight. The resulting reaction solution was concentrated under reduced pressure, and the obtained residue was purified by silica gel column chromatography to obtain 1.9 g (yield 65%) of the target product.

$^1$H-NMR of the obtained target product is shown below.
$^1$H-NMR (400 MHz, CDCl$_3$+D$_2$O*): δ 8.07 (m, 1H), 7.81 (m, 1H), 7.47 (s, 1H), 7.14 (m, 1H), 4.30 (q, 2H), 3.22 (q, 2H), 1.37 (t, 3H), 0.88 (t, 3H).

(*: Solvent in which one drop of D$_2$O was added to 0.7 ml of CDCl$_3$)

Step 1-4

Synthesis of 1-(2-(ethylsulfonyl)-4-(trifluoromethyl)phenyl)-1H-pyrazol-5-amine

[Chemical formula 14]

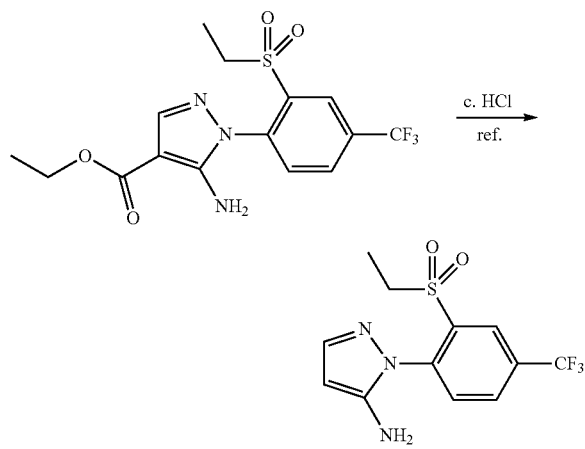

1.9 g (4.9 mmol) of ethyl 5-amino-1-(2-(ethylsulfonyl)-4-(trifluoromethyl) phenyl)-1H-pyrazole-4-carboxylate was dissolved in 14 ml of concentrated hydrochloric acid, and stirred under heating reflux for 5 hours. The resulting reaction solution was poured into water and neutralized by adding potassium carbonate, followed by extracting with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 1.1 g (yield 71%) of the target product.

$^1$H-NMR of the obtained target product is shown below.

$^1$H-NMR (400 MHz, CDCl$_3$): δ 8.46 (d, 1H), 8.03 (m, 1H), 7.59 (m, 1H), 7.52 (m, 1H), 5.69 (d, 1H), 3.81 (br s, 2H), 3.19 (q, 2H), 1.24 (t, 3H).

Step 1-5

Synthesis of 4-bromo-1-(2-(ethylsulfonyl)-4-(trifluoromethyl)phenyl)-1H-pyrazol-5-amine

[Chemical formula 15]

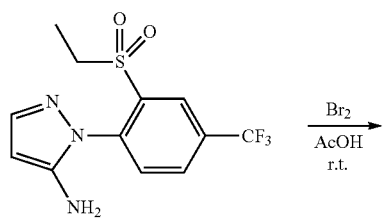

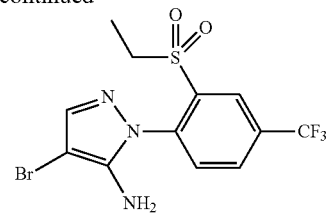

1.1 g (3.4 mmol) of 1-(2-(ethylsulfonyl)-4-(trifluoromethyl) phenyl)-1H-pyrazol-5-amine was dissolved in 10 ml of acetic acid and stirred at room temperature. Then, 0.55 g (0.55 g, 1.0 eq) of bromine was added dropwise thereto, and the resulting mixture was stirred at room temperature for 30 minutes. The resulting reaction solution was poured into water and neutralized by adding potassium carbonate, followed by extracting with ethyl acetate. The obtained organic layer was washed with saturated brine, dried over anhydrous magnesium sulfate, and filtered. The filtrate was concentrated under reduced pressure, and the obtained residue was washed with a mixed solvent of chloroform and normal hexane to obtain 1.2 (yield 86%) of the target product.

$^1$H-NMR of the obtained target product is shown below.

$^1$H-NMR (400 MHz, CDCl$_3$): δ 8.46 (m, 1H), 8.04 (m, 1H), 7.56 (m, 1H), 7.54 (s, 1H), 3.93 (br s, 2H), 3.20 (q, 2H), 1.24 (t, 3H).

Step 1-6

Synthesis of 1-(2-(ethylsulfonyl)-4-(trifluoromethyl)phenyl)-4-(4-(trifluoromethoxy)phenyl)-1H-pyrazol-5-amine (Compound No. 1-12)

[Chemical formula 16]

1.0 g (2.5 mmol) of 4-bromo-1-(2-(ethylsulfonyl)-4-(trifluoromethyl)phenyl)-1H-pyrazol-5-amine was dissolved in a mixed solvent of 6 ml of toluene and 2.2 ml of water, and stirred at room temperature. Then, 0.78 g (3.8 mmol, 1.5 eq) of paratrifluoromethoxyphenylboronic acid, 0.028 g (0.13 mmol, 5.0 mol %) of palladium (II) acetate, 0.12 g (0.25 mmol, 10 mol %) of X-phos and 1.1 g (5.0 mmol, 2.0 eq) of potassium phosphate were added thereto and stirred at 90° C. for 3 hours under an argon atmosphere. The resulting reaction solution was poured into water and followed by extracting with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.92 g (yield 77%) of the target product.

¹H-NMR of the obtained target product is shown below.

¹H-NMR (400 MHz, CDCl₃): δ 8.49 (m, 1H), 8.07 (m, 1H), 7.72 (s, 1H), 7.66 (m, 1H), 7.46 (m, 2H), 7.29 (m, 2H), 3.99 (br s, 2H), 3.27 (q, 2H), 1.26 (t, 3H).

Step 1-7

Synthesis of 5-chloro-1-(2-(ethylsulfonyl)-4-(trifluoromethyl)phenyl)-4-(4-(trifluoromethoxy)phenyl)-1H-pyrazole (Compound No. 1-17)

[Chemical formula 17]

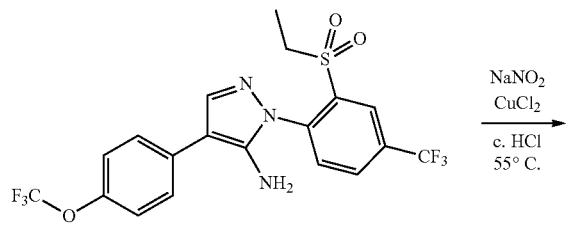

0.3 g (0.63 mmol) of 1-(2-(ethylsulfonyl)-4-(trifluoromethyl)phenyl)-4-(4-(trifluoromethoxy) phenyl)-1H-pyrazol-5-amine was dissolved in a concentrated hydrochloric acid and stirred at 0° C. Then, 0.052 g (0.75 mmol, 1.2 eq) of sodium nitrite was added thereto, and stirred at 0° C. for 1 hour. Then, 0.17 g (1.3 mmol, 2.0 eq) of copper (II) chloride was added thereto, and stirred at 55° C. overnight. The resulting reaction solution was poured into water and then extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.16 g (yield 51%) of the target product.

¹H-NMR of the obtained target product is shown below.

¹H-NMR (400 MHz, CDCl₃): δ 8.49 (m, 1H), 8.08 (m, 1H), 7.95 (s, 1H), 7.70-7.66 (m, 3H), 7.30 (m, 2H), 3.51 (q, 2H), 1.31 (t, 3H).

Example 2

Synthesis of 1-(2-(Ethylthio)-4-(trifluoromethyl)phenyl)-5-methyl-4-(4-(trifluoromethyl)phenyl)-1H-1,2,3-triazole (Compound No. 4-5) and 1-(2-(Ethylsulfonyl)-4-(trifluoromethyl)phenyl)-5-methyl-4-(4-(trifluoromethyl)phenyl)-1H-1,2,3-triazole (Compound No. 4-6)

Step 2-1

Synthesis of 1-Azido-2-chloro-4-(trifluoromethyl)benzene

[Chemical formula 18]

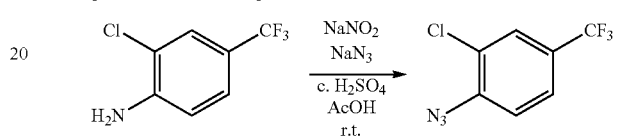

Sodium nitrite (0.85 g) as dissolved in a concentrated sulfuric acid (6 ml) and then acetic acid solution (12 ml) of 2-chloro-4-(trifluoromethyl) aniline (2.0 g) was added dropwise at 0° C. After raising the temperature to room temperature and stirring for 30 minutes, the resulting solution was cooled to 0° C., and then an aqueous solution (3 ml) of sodium azide (0.65 g) was added dropwise, and the resulting mixture was stirred at room temperature overnight. The reaction solution was poured into water and extracted with dichloroether. The obtained organic layer was washed with saturated sodium bicarbonate water and saturated brine, dried over anhydrous magnesium sulfate, and filtered. The filtrate was concentrated under reduced pressure, and the obtained residue was used in the next step without purification.

Step 2-2

Synthesis of 1-(2-Chloro-4-(trifluoromethyl)phenyl)-5-methyl-4-(4-(trifluoromethyl)phenyl)-1H-1,2,3-triazole

[Chemical formula 19]

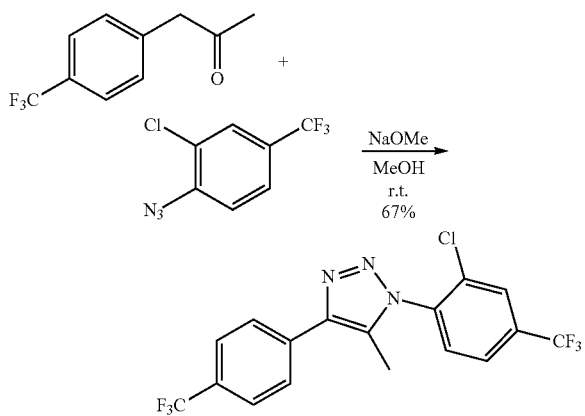

4-trifluoromethylphenylacetone (1.7 g) was dissolved in methanol (60 ml), and then the inside of the reaction vessel was replaced with nitrogen, followed by stirring at room temperature. Then, sodium methoxide (0.68 g) and 1-azido-2-chloro-4-(trifluoromethyl)benzene (ca. 10 mmol) which was prepared in Step 1-1 were added thereto, and stirred at room temperature overnight. The resulting reaction solution was poured into water and extracted with ethyl acetate. The obtained organic layer was washed with saturated brine, dried over anhydrous magnesium sulfate, and filtered. The filtrate was concentrated under reduced pressure, and the obtained residue was washed with n-hexane to obtain 2.3 g (yield 67%) of the target product.

$^1$H-NMR of the obtained target product is shown below.
$^1$H-NMR (400 MHz, CDCl$_3$): δ 7.95 (d, 2H), 7.92 (s, 1H), 7.78 (d, 1H), 7.75 (d, 2H), 7.66 (d, 1H), 2.42 (s, 3H).

Step 2-3

Synthesis of 1-(2-(Ethylthio)-4-(trifluoromethyl)phenyl)-5-methyl-4-(4-(trifluoromethyl)phenyl)-1H-1,2,3-triazole (Compound No. 4-5)

[Chemical formula 20]

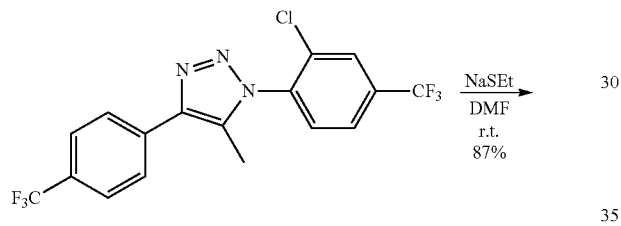

1-(2-chloro-4-(trifluoromethyl)phenyl)-5-methyl-4-(4-trifluoromethyl)phenyl)-1H-1,2,3-triazole (1.0 g) was dissolved in N-dimethylformamide (25 ml), and stirred at room temperature. Then, sodium ethyl mercaptan (80%, 0.31 g) was added thereto, followed by stirring at room temperature overnight. The resulting reaction solution was poured into water and then extracted with ethyl acetate. The obtained organic layer was washed with saturated brine, (hied over anhydrous magnesium sulfate, and filtered. The filtrate was concentrated under reduced pressure, and the obtained residue was purified by silica gel column chromatography to obtain 0.94 g (yield 87%) of the target product.

$^1$H-NMR of the obtained target product is shown below.

$^1$H-NMR (400 MHz, CDCl$_3$): δ 7.96 (d, 2H), 7.74 (d, 2H), 7.69 (s, 1H), 7.61 (d, 1H), 7.48 (d, 1H), 2.91 (q, 2H), 2.39 (s, 3H), 1.29 (t, 3H).

Step 2-4

Synthesis of 1-(2-(Ethylsulfonyl)-4-(trifluoromethyl)phenyl)-5-methyl-4-(4-(trifluoromethyl)phenyl)-1H-1,2,3-triazole (Compound No. 4-6)

[Chemical formula 21]

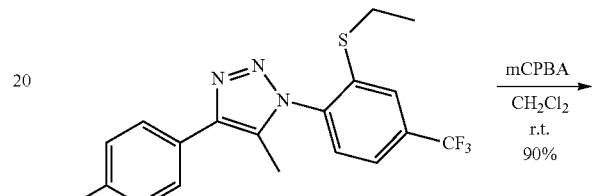

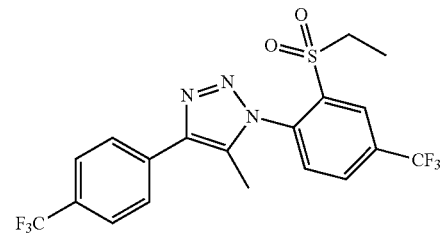

1-(2-(ethylthio)-4-(trifluoromethyl)phenyl)-5-methyl-4-(4-(trifluoromethyl)phenyl-1H-1,2,3-triazole (0.88 g) was dissolved in dichloromethane (2.0 ml), and stirred at 0° C. Then, methachloroperbenzoic acid (70%, 1.0 g) was added thereto and the resulting mixture was stirred overnight at room temperature. The resulting reaction solution was poured into a mixed solution of a saturated sodium hydrogen carbonate aqueous solution and a saturated sodium thiosulfate aqueous solution and extracted with dichloromethane. The obtained organic layer was washed with saturated brine, dried over anhydrous magnesium sulfate and filtered. The filtrate was concentrated under reduced pressure, and the resulting residue was purified by silica gel column chromatography to obtain 0.74 g (yield 90%) of the target product.

$^1$H-NMR of the obtained target product is shown below.

$^1$H-NMR (400 MHz, CDCl$_3$): δ 8.54 (s, 1H), 8.14 (d, 1H), 7.93 (d, 2H), 7.74 (d, 2H), 7.63 (d, 1H), 3.31 (q, 2H), 2.40 (s, 3H), 1.28 (t, 3H).

Example 3

Synthesis of 1-(2-(Ethylthio)-4-(trifluoromethyl)phenyl)-4-(4-(trifluoromethoxy)phenyl)-1H-1,2,3-triazole (Compound No. 4-7) and 1-(2-(Ethylsulfonyl)-4-(trifluoromethyl)phenyl)-4-(4-(trifluoromethoxy)phenyl)-1H-1,2,3-triazole (Compound No. 4-8)

Step 3-1

Synthesis of 1-Azido-2-fluoro-4-(trifluoromethyl)benzene

[Chemical formula 22]

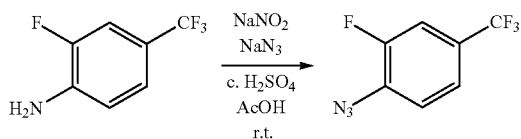

Sodium nitrite (1.2 s dissolved in a concentrated sulfuric acid (9 ml), and then acetic acid solution (18 ml) of 2-fluoro-4-(trifluoromethyl) aniline (2.8 g) was added dropwise at 0° C. After raising the temperature to room temperature and stirring for 30 minutes, the resulting solution was cooled to 0° C., and then an aqueous solution (3 ml) of sodium azide (0.98 g) was added dropwise, followed by stirring at room temperature overnight. The resulting reaction solution was poured into water and extracted with dichloroether. The obtained organic layer was washed with saturated sodium bicarbonate water and saturated brine, dried over anhydrous magnesium sulfate, and filtered. The filtrate was concentrated under reduced pressure, and the obtained residue was used in the next step without purification.

Step 3-2

Synthesis of 1-(2-Fluoro-4-(trifluoromethyl)phenyl)-4-(4-(trifluoromethoxy)phenyl)-1H-1,2,3-triazole

[Chemical formula 23]

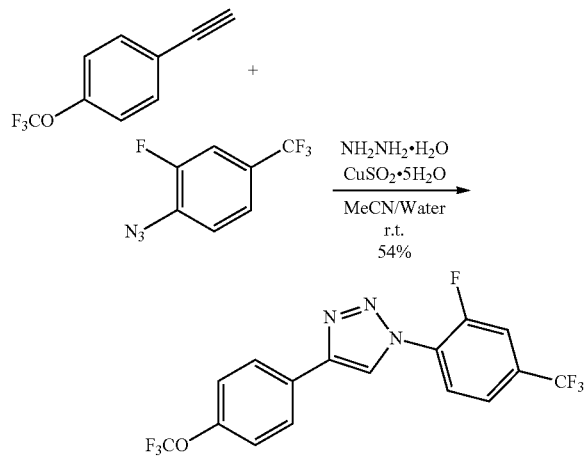

1-azide-2-fluoro-4-(trifluoromethyl)benzene (ca. 5.0 mmol) prepared in Step 3-1 was dissolved in a mixed solvent of acetonitrile (10 ml) and water (20 ml), followed by stirring. Then, 1-ethynyl-4-(trifluoromethoxy)benzene (1.0 g), copper sulfate pentahydrate (0.12 g) and hydrazine hydrate (0.25 g) were added thereto, and stirred at room temperature for 2 hours. The resulting reaction solution was poured into water and then extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 1.1 g (yield 54%) of target product.

$^1$H-NMR of the obtained target product is shown below.

$^1$H-NMR (400 MHz, CDCl$_3$): δ 8.38 (d, 1H), 8.28 (t, 1H), 7.95 (m, 2H), 7.65 (d, 1H), 7.62 (d, 1H), 7.32 (d, 2H).

Step 3-3

Synthesis of 1-(2-(Ethylthio)-4-(trifluoromethyl)phenyl)-4-(4-(trifluoromethoxy)phenyl)-1H-1,2,3-triazole (Compound No. 4-7)

[Chemical formula 24]

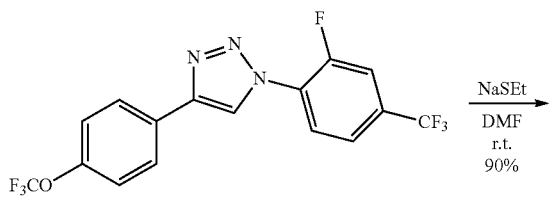

1-(2-fluoro-4-(trifluoromethyl) phenyl)-4-(4-(trifluoromethoxy)phenyl)-1H-1,2,3-triazole (1.0 g) was dissolved in formamide (10 ml) and stirred at room temperature. Then, sodium ethyl mercaptan (80%, 0.31 g) was added thereto, and the resulting mixture was stirred at room temperature overnight. The reaction solution was poured into water and then extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.96 g (yield 90%) of the target product.

$^1$H-NMR of the obtained target product is shown below.

$^1$H-NMR (400 MHz, CDCl$_3$): δ 8.22 (s, 1H), 7.95 (m, 2H), 7.10 (d, 1H), 7.67 (d, 1H), 7.61 (dd, 1H), 7.32 (d, 2H), 2.90 (q, 2H), 1.27 (t, 3H).

Step 3-4

Synthesis of 1-(2-(Ethylsulfonyl)-4-(trifluoromethyl)phenyl)-4-(4-(trifluoromethoxy)phenyl)-1H-1,2,3-triazole (Compound No. 4-8)

[Chemical formula 25]

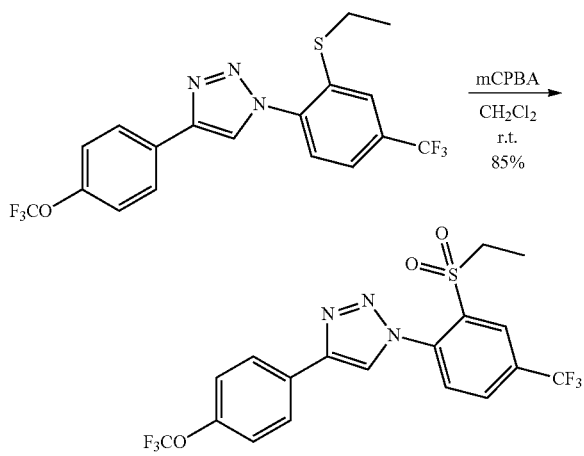

1-(2-(ethylthio)-4-(trifluoromethyl) phenyl)-4-(4-(trifluoromethoxy) phenyl)-1H-1,2,3-triazole (0.70 g) was dissolved in dichloromethane (10 ml), and stirred at 0° C. Then, methachloroperbenzoic acid (70%, 0.87 g) was added thereto, and the resulting mixture was stirred at room temperature overnight. The reaction solution was poured into a mixed solution of saturated sodium hydrogen carbonate aqueous solution and saturated sodium thiosulfate aqueous solution, and extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 0.64 g (yield: 85%) of the target product.

$^1$H-NMR of the obtained target product is shown below.

$^1$H-NMR (400 MHz, CDCl$_3$): δ 8.53 (d, 1H), 8.24 (s, 1H), 8.10 (dd, 1H), 7.94 (m, 2H), 7.73 (d, 1H), 7.32 (d, 2H), 3.21 (q, 2H), 1.27 (t, 3H).

The compounds of the present invention prepared by the same method as in the above examples are shown in TABLES 1 to 6. TABLE 1 shows the substituents on the compounds represented by formula (II-1). TABLE 2 shows the substituents on the compounds represented by formula (II-2). TABLE 3 shows the substituents on the compounds represented by formula. (III-1). TABLE 4 shows the substituents on the compounds represented by formula (IV-1). TABLE 5 shows the substituents on the compounds represented by formula (V-1). The physical property data of the compounds was described in the column of "Physical Property". As the physical property data, properties, melting point (m.p.), or refractive index (n$_D$) are described. Abbreviations in the table, such as Me represents a methyl group, Et represents an ethyl group, and tBu represents a tertiary butyl group.

[Chemical formula 26]

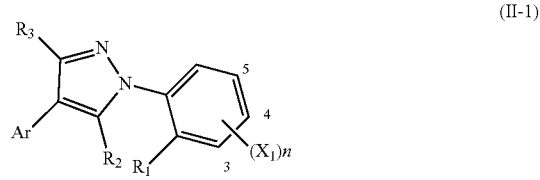

(II-1)

TABLE 1

| Compound No. | (X$^1$)n | R$^1$ | R$^2$ | R$^3$ | Ar | Physical Property |
|---|---|---|---|---|---|---|
| 1-1 | 4-CF$_3$ | SEt | H | H | 4-CF$_3$-phenyl | m.p.: 88-90 (° C.) |
| 1-2 | 4-CF$_3$ | SO$_2$Et | H | H | 4-CF$_3$-phenyl | m.p.: 161-163 (° C.) |
| 1-3 | 4-CF$_3$ | SOEt | H | H | 4-CF$_3$-phenyl | m.p.: 158-160 (° C.) |
| 1-4 | 4-CF$_3$ | SEt | NH$_2$ | H | 4-CF$_3$-phenyl | m.p.: 103-105 (° C.) |
| 1-5 | 4-CF$_3$ | SO$_2$Et | NH$_2$ | H | 4-CF$_3$-phenyl | m.p.: 224-228 (° C.) |
| 1-6 | 4-CF$_3$ | SEt | H | H | 2-Me-4-CF$_3$-phenyl | m.p.: 55-57 (° C.) |
| 1-7 | 4-CF$_3$ | SO$_2$Et | H | H | 2-Me-4-CF$_3$-phenyl | Amorphous |
| 1-8 | 4-CF$_3$ | SEt | Me | H | 4-CF$_3$-phenyl | m.p.: 97-99 (° C.) |
| 1-9 | 4-CF$_3$ | SOEt | Me | H | 4-CF$_3$-phenyl | m.p.: 123-127 (° C.) |
| 1-10 | 4-CF$_3$ | SO$_2$Et | Me | H | 4-CF$_3$-phenyl | m.p.: 183-185 (° C.) |
| 1-11 | 4-CF$_3$ | SO$_2$Et | N(C(=O)O$^t$Bu)$_2$ | H | 4-OCF$_3$-phenyl | m.p.: 152-154 (° C.) |
| 1-12 | 4-CF$_3$ | SO$_2$Et | NH$_2$ | H | 4-OCF$_3$-phenyl | m.p.: 153-157 (° C.) |
| 1-13 | 4-CF$_3$ |  | *SO$_2$—**CH(CH$_3$) | H | 4-OCF$_3$-phenyl | m.p.: 177-181 (° C.) |
| 1-14 | 4-CF$_3$ | SO$_2$Et | H | H | 4-OCF$_3$-phenyl | m.p.: 131-133 (° C.) |
| 1-15 | 4-CF$_3$ | SO$_2$Et | H | H | 6-CF$_3$-pyridin-3-yl | m.p.: 142-144 (° C.) |
| 1-16 | 4-CF$_3$ | SO$_2$Et | H | H | 2-F-4-CF$_3$-phenyl | m.p.: 129-131 (° C.) |
| 1-17 | 4-CF$_3$ | SO$_2$Et | Cl | H | 4-OCF$_3$-phenyl | m.p.: 146-150 (° C.) |
| 1-18 | 4-CF$_3$ | SH | Me | H | 4-OCF$_3$-phenyl | m.p.: 152-154 (° C.) |
| 1-19 | 4-CF$_3$ | SO$_2$Et | Me | H | 4-OCF$_3$-phenyl | m.p.: 144-146 (° C.) |
| 1-20 | 4-CF$_3$ | SO$_2$Et | Br | H | 4-OCF$_3$-phenyl | m.p.: 141-143 (° C.) |
| 1-21 | 4-CF3 | SO$_2$Et | CN | H | 4-OCF$_3$-phenyl | nD(24.9)1.5328 |
| 1-22 | 4-CF$_3$ | SO$_2$Et | H | H | 4-CF$_2$CF$_3$-phenyl | m.p.: 172-174 (° C.) |
| 1-23 | 4-CF$_3$ | SO$_2$Et | F | H | 4-OCF$_3$-phenyl | m.p.: 168-170 (° C.) |
| 1-24 | 4-CF$_3$ | SO$_2$Et | Me | H | 6-CF$_3$-pyridin-3-yl | m.p.: 168-170 (° C.) |
| 1-25 | 4-CF$_3$ | SO$_2$Et | NH$_2$ | H | 6-CF$_3$-pyridin-3-yl | m.p.: 197-199 (° C.) |
| 1-26 | 4-CF$_3$ | SO$_2$Et | Me | H | 3,5-(CF$_3$)$_2$-phenyl | m.p.: 142-144 (° C.) |
| 1-27 | 4-CF$_3$ | SO$_2$Et | H | H | 3,5-(CF$_3$)$_2$-phenyl | m.p.: 163-165 (° C.) |
| 1-28 | 4-CF$_3$ | SO$_2$Et | NH$_2$ | H | 3,5-(CF$_3$)$_2$-phenyl | m.p.: 158-162 (° C.) |
| 1-29 | 4-CF$_3$ |  | *SO$_2$—**CH(CH$_3$) | H | 3,5-(CF$_3$)$_2$-phenyl | m.p.: 204-206 (° C.) |
| 1-30 | 4-CF$_3$ | SO$_2$Et | I | H | 3,5-(CF$_3$)$_2$-phenyl | m.p.: 159-163 (° C.) |

TABLE 1-continued

| Compound No. | (X¹)n | R¹ | R² | R³ | Ar | Physical Property |
|---|---|---|---|---|---|---|
| 1-31 | 4-CF₃ | SO₂Et | NH₂ | H | 4-C₂F₅-phenyl | m.p.: 138-141 (° C.) |
| 1-32 | 4-CF₃ | SO₂Et | NH₂ | H | 4-SCF₃-phenyl | viscous oil |
| 1-33 | 4-CF₃ | SO₂Et | NH₂ | H | 6-C₂F₅-pyridin-3-yl | m.p.: 155-159 (° C.) |
| 1-34 | 4-CF₃ | SO₂Et | NH₂ | H | 3-OCF₃-phenyl | amorphous |
| 1-35 | 4-CF₃ | SO₂Et | NH₂ | H | 4-(perfluoropropan-2-yl)phenyl | amorphous |
| 1-36 | 4-CF₃ | SO₂Et | NH₂ | H | 3-Cl-4-CF₃-phenyl | m.p.: 168-170 (° C.) |
| 1-37 | 4-CF₃ | SO₂Et | NH₂ | H | 3-(3-Cl-4-CF₃-phenyl)-4-CF₃-phenyl | viscous oil |
| 1-38 | 4-CF₃ | SO₂Et | NH₂ | H | 3-Cl-4-OCF₃-phenyl | amorphous |
| 1-39 | 4-CF₃ | SO₂Et | NH₂ | H | 3-(3-Cl-4-CF₃-phenyl)-4-OCF3-phenyl | amorphous |
| 1-40 | 4-CF₃ | SO₂Et | H | Me | 4-OCF₃-phenyl | $n_D(20.6)1.5314$ |
| 1-41 | 4-CF₃ | SO₂Et | H | Me | 6-CF₃-pyridin-3-yl | m.p.: 80-82 (° C.) |
| 1-42 | 4-CF₃ | SO₂Et | NH(C(=O)OᵗBu) | H | 4-OCF₃-phenyl | m.p.: 163-164 (° C.) |
| 1-43 | 4-CF₃ | SO₂Et | NMe(C(=O)OᵗBu) | H | 4-OCF₃-phenyl | m.p.: 136-138 (° C.) |
| 1-44 | 4-CF₃ | SO₂Et | NHMe | H | 4-OCF₃-phenyl | m.p.: 129-131 (° C.) |
| 1-45 | 4-CF₃ | SO₂Et | N(CH₂OMe)(C(=O)OᵗBu) | H | 4-OCF₃-phenyl | m.p.: 134-137 (° C.) |
| 1-46 | 4-CF₃ | SO₂Et | H | H | 3,5-(CF₃)₂—1H-pyrazol-1-yl | White solid |
| 1-47 | 4-CF₃ | SO₂Et | Me | H | 6-C₂F₅-pyridin-3-yl | viscous oil |
| 1-48 | 4-CF₃ | SO₂Et | H | H | 1H-pyrazol-1-yl | m.p.: 135-138 (° C.) |
| 1-49 | 4-CF₃ | SO₂Et | H | H | 4-I—1H-pyrazol-1-yl | m.p.: 142-146 (° C.) |
| 1-50 | 4-CF₃ | SO₂Et | H | H | 4-CF₃—1H-pyrazol-1-yl | m.p.: 131-134 (° C.) |
| 1-51 | 4-CF₃ | SO₂Et | H | H | 4-C₂F₅—1H-pyrazol-1-yl | m.p.: 134-136 (° C.) |
| 1-52 | 4-CF₃ | SO₂Et | CN | H | 6-C₂F₅-pyridin-3-yl | m.p.: 160-163 (° C.) |
| 1-53 | 5-F | SO₂Et | NH₂ | H | 4-OCF₃-phenyl | m.p.: 128-130 (° C.) |
| 1-54 | 5-(1H-1,2,4-triazol-1-yl) | SO₂Et | NH₂ | H | 4-OCF₃-phenyl | m.p.: 220-222 (° C.) |
| 1-55 | 5-(1H-1,2,4-triazol-1-yl) | SO₂Et | Br | H | 4-OCF₃-phenyl | m.p.: 137-139 (° C.) |
| 1-56 | 5-(1H-1,2,4-triazol-1-yl) | SO₂Et | Me | H | 4-OCF₃-phenyl | m.p.: 141-143 (° C.) |

(In the table, the sulfur atom marked with * is bonded to the carbon atom to which R¹ is bonded, and the carbon atom marked with ** is bonded to the carbon atom to which R² is bonded.)

[Chemical formula 27]

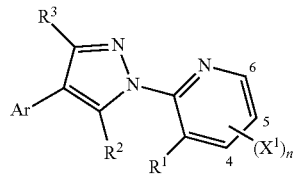

(II-2)

TABLE 2

| Compound No. | (X¹)n | R¹ | R² | R³ | Ar | Physical Property |
|---|---|---|---|---|---|---|
| 2-1 | 5-CF₃ | SO₂Et | H | H | 4-CF₃-phenyl | m.p.: 173-175 (° C.) |
| 2-2 | 5-CF₃ | SO₂Et | NH₂ | H | 4-CF₃-phenyl | m.p.: 200-201 (° C.) |
| 2-3 | 5-CF₃ | SO₂CH(Br)CH₃ | H | H | 4-CF₃-phenyl | m.p.: 200-201 (° C.) |
| 2-4 | 5-CF₃ | SO₂Et | NH₂ | H | 4-OCF₃-phenyl | m.p.: 165-168 (° C.) |
| 2-5 | 5-CF₃ | SO₂Et | Me | H | 6-CF₃-pyridin-3-yl | m.p.: 160-162 (° C.) |
| 2-6 | 5-CF₃ | SO₂Et | H | H | 4-OCF₃-phenyl | amorphous |
| 2-7 | 5-CF₃ | SO₂Et | Me | H | 4-OCF₃-phenyl | amorphous |
| 2-8 | — | SO₂Et | Me | H | 4-OCF₃-phenyl | m.p.: 133-136 (° C.) |
| 2-9 | — | SO₂Et | Me | H | 4-C₂F₅-phenyl | m.p.: 132-135 (° C.) |
| 2-10 | — | SO₂Et | NH₂ | H | 4-OCF₃-phenyl | m.p.: 143-146 (° C.) |
| 2-11 | — | SO₂Et | NH₂ | H | 4-C₂F₅-phenyl | m.p.: 162-165 (° C.) |
| 2-12 | — | SO₂Et | NH₂ | H | 4-SCF₃-phenyl | m.p.: 164-167 (° C.) |
| 2-13 | — | SO₂Et | NH₂ | H | 4-SC₂F₅-phenyl | m.p.: 146-149 (° C.) |
| 2-14 | — | SO₂Et | NH₂ | H | 6-C₂F₅-pyridin-3-yl | m.p.: 210-214 (° C.) |
| 2-15 | — | SO₂Et | Br | H | 6-C₂F₅-pyridin-3-yl | m.p.: 168-170 (° C.) |
| 2-16 | — | SO₂Et | Me | H | 6-C₂F₅-pyridin-3-yl | m.p.: 155-157 (° C.) |

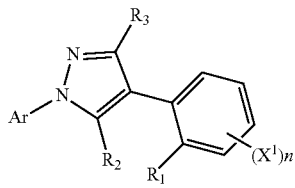

(III-1)

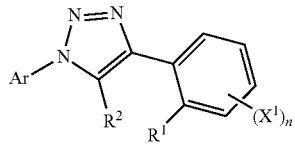

(V-1)

TABLE 3

| Compound No. | $(X^1)n$ | $R^1$ | $R^2$ | $R^3$ | Ar | Physical Property |
|---|---|---|---|---|---|---|
| 3-1 | 4-$CF_3$ | $SO_2Et$ | $NH_2$ | H | 4-$CF_3$-phenyl | m.p.: 184-186 (° C.) |
| 3-2 | 4-$CF_3$ | $SO_2Et$ | Cl | H | 4-$CF_3$-phenyl | viscous oil |
| 3-3 | 4-$CF_3$ | $SO_2Et$ | Br | H | 4-$CF_3$-phenyl | viscous oil |
| 3-4 | 4-$CF_3$ | $SO_2Et$ | I | H | 4-$CF_3$-phenyl | m.p.: 144-147 (° C.) |
| 3-5 | 4-$CF_3$ | $SO_2Et$ | Me | H | 4-$CF_3$-phenyl | m.p.: 97-100 (° C.) |
| 3-6 | 4-$CF_3$ | $SO_2Et$ | H | H | 4-$CF_3$-phenyl | m.p.: 149-151 (° C.) |
| 3-7 | 4-$CF_3$ | $SO_2Et$ | $NH_2$ | H | 4-$OCF_3$-phenyl | m.p.: 167-169 (° C.) |
| 3-8 | 4-$CF_3$ | $SO_2Et$ | $N(COMe)_2$ | H | 4-$OCF_3$-phenyl | m.p.: 150-152 (° C.) |
| 3-9 | 4-$CF_3$ | $SO_2Et$ | NH(COMe) | H | 4-$OCF_3$-phenyl | viscous oil |
| 3-10 | 4-$CF_3$ | $SO_2Et$ | Me | H | 4-$OCF_3$-phenyl | viscous oil |

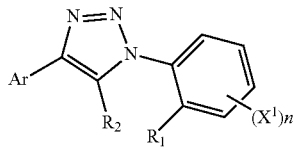

(IV-1)

TABLE 5

| Compound No. | $(X^1)n$ | $R^1$ | $R^2$ | Ar | Physical Property |
|---|---|---|---|---|---|
| 5-1 | 4-$CF_3$ | SEt | H | 4-$OCF_3$-phenyl | m.p.: 107-108 (° C.) |
| 5-2 | 4-$CF_3$ | $SO_2Et$ | H | 4-$OCF_3$-phenyl | m.p.: 167-168 (° C.) |
| 5-3 | 4-$CF_3$ | SEt | Me | 4-$OCF_3$-phenyl | m.p.: 73-74 (° C.) |

TABLE 4

| Compound No. | $(X^1)n$ | $R^1$ | $R^2$ | Ar | Physical Property |
|---|---|---|---|---|---|
| 4-1 | 4-$CF_3$ | SEt | Me | 4-$OCF_3$-phenyl | m.p.: 112-113 (° C.) |
| 4-2 | 4-$CF_3$ | $SO_2Et$ | Me | 4-$OCF_3$-phenyl | m.p.: 170-172 (° C.) |
| 4-3 | 4-$CF_3$ | $SO_2Et$ | Me | 4-OH-phenyl | m.p.: 223-225 (° C.) |
| 4-4 | 4-$CF_3$ | $SO_2Et$ | Me | 4-((3-Cl-5-$CF_3$-pyridin-2-yl)O)phenyl | viscous oil |
| 4-5 | 4-$CF_3$ | SEt | Me | 4-$CF_3$-phenyl | m.p.: 79-80 (° C.) |
| 4-6 | 4-$CF_3$ | $SO_2Et$ | Me | 4-$CF_3$-phenyl | m.p.: 154-156 (° C.) |
| 4-7 | 4-$CF_3$ | SEt | H | 4-$OCF_3$-phenyl | m.p.: 110-111 (° C.) |
| 4-8 | 4-$CF_3$ | $SO_2Et$ | H | 4-$OCF_3$-phenyl | m.p.: 178-179 (° C.) |
| 4-9 | 4-$CF_3$ | SEt | Me | 4-$OCF_3$-phenyl | m.p.: 105-106 (° C.) |
| 4-10 | 4-$CF_3$ | $SO_2Et$ | Me | 4-$OCF_3$-phenyl | m.p.: 161-162 (° C.) |
| 4-11 | 4-$CF_3$ | SEt | $NH_2$ | 4-$OCF_3$-phenyl | m.p.: 159-160 (° C.) |
| 4-12 | 4-$CF_3$ | $SO_2Et$ | $NH_2$ | 4-$OCF_3$-phenyl | m.p.: 147-148 (° C.) |
| 4-13 | 4-$CF_3$ | SEt | Me | 6-$CF_3$-pyridin-3-yl | m.p.: 81-82 (° C.) |
| 4-14 | 4-$CF_3$ | SOEt | Me | 6-$CF_3$-pyridin-3-yl | m.p.: 155-156 (° C.) |
| 4-15 | 4-$CF_3$ | $SO_2Et$ | Me | 6-$CF_3$-pyridin-3-yl | m.p.: 181-182 (° C.) |
| 4-16 | 4-$CF_3$ | SEt | H | 3-Br-4-$OCF_3$-phenyl | viscous oil |
| 4-17 | 4-$CF_3$ | $SO_2Et$ | H | 3-Br-4-$OCF_3$-phenyl | m.p.: 148-150 (° C.) |
| 4-18 | 5-F | SEt | H | 4-$OCF_3$-phenyl | $n_D(22.2)1.5689$ |
| 4-19 | 5-F | $SO_2Et$ | H | 4-$OCF_3$-phenyl | viscous oil |
| 4-20 | 5-(1H-1,2,4-triazol-1-yl) | $SO_2Et$ | H | 4-$OCF_3$-phenyl | m.p.: 173-175 (° C.) |
| 4-21 | 5-(1H-pyrazol-1-yl) | $SO_2Et$ | H | 4-$OCF_3$-phenyl | m.p.: 155-159 (° C.) |
| 4-22 | 5-(4-Br-1H-pyrazol-1-yl) | $SO_2Et$ | H | 4-$OCF_3$-phenyl | m.p.: 120-123 (° C.) |
| 4-23 | 5-$NMe_2$ | $SO_2Et$ | H | 4-$OCF_3$-phenyl | m.p.: 173-175 (° C.) |
| 4-24 | 5-(4-Cl-phenyl)O | $SO_2Et$ | H | 4-$OCF_3$-phenyl | $n_D(21.8)1.5716$ |
| 4-25 | 5-$OCH_2CF_2CHF_2$ | $SO_2Et$ | H | 4-$OCF_3$-phenyl | amorphous |

TABLE 5-continued

| Compound No. | (X¹)n | R¹ | R² | Ar | Physical Property |
|---|---|---|---|---|---|
| 5-4 | 4-CF₃ | SO₂Et | Me | 4-OCF₃-phenyl | m.p.: 184-185 (° C.) |

TABLE 6

| Compound No. | Structure | Physical Property |
|---|---|---|
| 6-1 | Mixture | m.p.: 110-120 (° C.) |

¹H-NMR data (400 MHz, CDCl₃) is shown in TABLE 7 for several compounds among the compounds listed in the above TABLE 1 to TABLE 6.

specification, that is, those compounds substituted by various groups without departing from the spirit and scope of the present invention, can be produced by the above method and the like, and used.

[Biological Test]

The following test examples show that the diarylazole compound of the present invention (hereinafter, referred to as the compound of the present invention) is useful as an active ingredient of a harmful organism control agent and an external parasite control agent. "Parts" is by weight.

TABLE 7

| Compound No. | NMR data (ppm) |
|---|---|
| 1-7 | 8.52 (s, 1H), 8.08 (s, 1H), 8.04 (m, 1H), 7.95 (s, 1H), 7.75 (d, 1H), 7.55-7.51 (m, 3H), 3.22 (q, 2H), 2.52 (s, 3H), 1.26 (t, 3H). |
| 1-32 | 8.49 (d, 1H), 8.07 (dd, 1H), 7.77 (s, 1H), 7.71 (m, 2H), 7.66 (d, 1H), 7.50 (m, 2H), 4.06 (br s, 2H), 3.28 (q, 2H), 1.27 (t, 3H). |
| 1-34 | 8.49 (d, 1H), 8.07 (dd, 1H), 7.74 (s, 1H), 7.66 (d, 1H), 7.45 (d, 1H), 7.37 (m, 1H), 7.20 (m, 1H), 7.13 (m, 1H), 4.02 (br s, 2H), 3.28 (q, 2H), 1.27 (t, 3H). |
| 1-35 | 8.50 (d, 1H), 8.08 (dd, 1H), 7.78 (s, 1H), 7.67 (m, 2H), 7.66 (s, 1H), 7.58 (m, 2H), 4.06 (br s, 2H), 3.28 (q, 2H), 1.27 (t, 3H). |
| 1-37 | 8.50 (d, 1H), 8.08 (dd, 1H), 7.82 (d, 1H), 7.78 (s, 1H), 7.76 (d, 1H), 7.65 (d, 1H), 7.60 (m, 1H), 7.54 (s, 1H), 7.38 (d, 1H), 7.36 (d, 1H), 4.05 (br s, 2H), 3.29 (q, 2H), 1.27 (t, 3H). |
| 1-38 | 8.49 (d, 1H), 8.08 (dd, 1H), 7.71 (s, 1H), 7.65 (d, 1H), 7.56 (d, 1H), 7.40-7.34 (m, 2H), 4.00 (br s, 2H), 3.28 (q, 2H), 1.27 (t, 3H). |
| 1-39 | 8.50 (d, 1H), 8.08 (dd, 1H), 7.45 (s, 1H), 7.66 (d, 1H), 7.61 (d, 1H), 7.49 (m, 1H), 7.46-7.41 (m, 4H), 7.36 (d, 1H), 4.00 (br s, 2H), 3.29 (q, 2H), 1.27 (t, 3H). |
| 1-46 | 8.48 (d, 1H), 8.00 (dd, 1H), 7.93 (d, 1H), 7.80 (d, 1H), 7.65 (d, 1H), 3.19 (q, 2H), 1.23 (t, 3H). |
| 1-47 | 8.88 (s, 1H), 8.51 (s, 1H), 8.09 (d, 1H), 7.96 (d, 1H), 7.91 (s, 1H), 7.77 (d, 1H), 7.62 (d, 1H), 3.40 (q, 2H), 2.32 (s, 3H), 1.28 (t, 3H). |
| 2-6 | 8.92 (d, 1H), 8.83 (d, 1H), 8.65 (s, 1H), 8.10 (s, 1H), 7.62-7.59 (m, 2H), 7.30-7.26 (m, 2H), 4.10 (q, 2H), 1.46 (t, 3H). |
| 2-7 | 9.04 (d, 1H), 8.79 (d, 1H), 7.82 (s, 1H), 7.50-7.45 (m, 2H), 7.32-7.27 (m, 2H), 3.89 (q, 2H), 2.49 (s, 3H), 1.41 (t, 3H). |
| 3-2 | 8.51 (s, 1H), 8.03 (s, 1H), 7.96 (d, 1H), 7.82 (m, 4H), 7.63 (d, 1H), 2.91 (q, 2H), 1.54 (s, 3H), 1.16 (t, 3H). |
| 3-3 | 8.50 (d, 1H), 8.03 (s, 1H), 7.96 (dd, 1H), 7.81 (m, 4H), 7.61 (d, 1H), 2.89 (q, 2H), 2.03 (s, 3H), 1.16 (t, 3H). |
| 3-9 | 8.48 (d, 1H), 7.97-7.93 (m, 2H), 7.70 (s, 1H), 7.65 (d, 1H), 7.63-7.60 (m, 2H), 7.33 (m, 2H), 2.95 (q, 2H), 1.89 (s, 3H), 1.15 (t, 3H). |
| 3-10 | 8.52 (d, 1H), 7.93 (dd, 1H), 7.74 (s, 1H), 7.60-7.56 (m, 2H), 7.55 (d, 1H), 7.38 (m, 2H), 2.92 (q, 2H), 2.24 (s, 3H), 1.15 (t, 3H). |
| 4-4 | 8.55 (d, 1H), 8.30 (m, 1H), 8.15 (dd, 1H), 8.01 (d, 1H), 7.90 (m, 2H), 7.64 (d, 1H), 7.32 (m, 2H), 3.33 (q, 2H), 2.41 (s, 3H), 1.29 (t, 3H). |
| 4-16 | 8.17-8.14 (m, 2H), 7.74 (d, 1H), 7.64 (dd, 1H), 7.51 (d, 1H), 7.38-7.34 (m, 2H), 2.96 (q, 2H), 1.30 (t, 3H). |
| 4-19 | 8.30 (dd, 1H), 8.23 (s, 1H), 7.94 (m, 2H), 7.50 (m, 1H), 7.35-7.30 (m, 3H), 3.16 (q, 2H), 2.32 (s, 3H), 1.24 (t, 3H). |
| 4-25 | 8.23 (s, 1H), 8.22 (d, 1H), 7.96-7.90 (m, 2H), 7.34-7.28 (m, 3H), 7.13 (d, 1H), 6.03 (tt, 1H), 4.51 (t, 2H), 3.12 (q, 2H), 2.32 (s, 3H), 1.23 (t, 3H). |

As described above, the diarylazole compound of the present invention can be easily produced by using known chemical reactions as in the above examples. It is easily understood by those skilled in the art that other compounds which could not be specifically mentioned in the present (Preparation of Test Emulsion)

5 parts of the compound of the present invention, 93.6 parts of dimethylformamide, and 1.4 parts of polyoxyethylene alkylaryl ether were mixed and dissolved to prepare an emulsion (I) of 5% of the active ingredient.

The insect mortality rate and the control rate were calculated by the following formula.

Insect mortality rate (%)=(number of dead insects/number of sample insects)×100

Prevention rate=[1−(Nt)/(Nc)]×100

Nt: number of parasites in spray-treatment area
Nc: number of parasites in control area (Test Example 1) Efficacy Test Against *Pseudaletia Separate*

0.8 g of commercially available artificial diet (Insecta US, manufactured by Nosan Corporation) and 1 μl of emulsion (1) were well mixed and 0.2 g of the resulting mixture was packed in a plastic test container (1.4 ml) per each treatment group to prepare test feeds.

2 second-instar larvae of *Pseudaletia separata* were inoculated into each treatment group and sealed with a plastic lid. The plastic test containers were placed in a thermostatic chamber with a temperature of 25° C., and the insect mortality rate and the food intake amount were investigated on the fifth day. The test was repeated twice.

Further, a test under the same conditions except that the compound of the present invention was removed from emulsion (I) was conducted as a solvent control group.

Efficacy test against *Pseudaletia separate* was carried out for the compounds shown in TABLE 8. All of the compounds were effective and demonstrated 100% of insect mortality rate, 10% or less of food intake amount in ratio to the solvent control group against *Pseudaletia separata*.

TABLE 8

| Compound No. | | | |
|---|---|---|---|
| 1-1 | 1-25 | 1-47 | 2-9 |
| 1-2 | 1-26 | 1-49 | 2-10 |
| 1-4 | 1-27 | 1-50 | 2-11 |
| 1-5 | 1-28 | 1-51 | 2-12 |
| 1-9 | 1-30 | 1-52 | 2-16 |
| 1-12 | 1-31 | 1-53 | 3-1 |
| 1-14 | 1-32 | 1-54 | 3-2 |
| 1-15 | 1-33 | 1-55 | 3-3 |
| 1-16 | 1-34 | 1-56 | 3-4 |
| 1-17 | 1-35 | 2-2 | 3-5 |
| 1-19 | 1-36 | 2-4 | 5-1 |
| 1-20 | 1-38 | 2-5 | 5-2 |
| 1-22 | 1-40 | 2-6 | 5-3 |
| 1-23 | 1-41 | 2-7 | 6-1 |
| 1-24 | 1-44 | 2-8 | |

(Test Example 2) Efficacy Test Against *Spodoptera litura*

Emulsion (I) was diluted with water so that the concentration of the compound of the present invention reaches 125 ppm. Cabbage leaves were soaked in the diluted liquid for 30 seconds. Then the cabbage leaves were put on Petri dishes, followed by inoculating 5 second-instar larvae of *Spodoptera litura*. The Petri dishes were placed in a thermostatic chamber with a temperature was 25° C. and a humidity of 60%. Life or death judgement was performed after 6 days were passed, and the insect mortality rate was calculated. The test was repeated twice.

Efficacy test against *Spodoptera litura* was carried out for the compounds shown in TABLE 9. All of the compounds demonstrated 80% or more of insect mortality rate against *Spodoptera litura*.

TABLE 9

| Compound No. | | | |
|---|---|---|---|
| 1-1 | 1-19 | 1-32 | 2-4 |
| 1-2 | 1-20 | 1-33 | 2-5 |
| 1-4 | 1-22 | 1-35 | 2-6 |
| 1-5 | 1-23 | 1-36 | 2-7 |
| 1-10 | 1-24 | 1-38 | 2-13 |
| 1-12 | 1-26 | 1-47 | 3-3 |
| 1-14 | 1-27 | 1-50 | 5-2 |
| 1-15 | 1-28 | 1-51 | |
| 1-16 | 1-30 | 1-52 | |
| 1-17 | 1-31 | 2-1 | |

(Test Example 3) Efficacy Test Against *Plutella xylostella*

Emulsion (I) was diluted with water so that the concentration of the compound of the present invention reaches 125 ppm. Cabbage leaves were soaked in the diluted liquid for 30 seconds. Then the cabbage leaves were put on Petri dishes, followed by inoculating 5 second-instar larvae of *Plutella xylostella*. The Petri dishes were placed in a thermostatic chamber with a temperature was 25° C. and a humidity of 60%. Life or death judgement was performed after 3 days were passed, and the insect mortality rate was calculated. The test was repeated twice.

Efficacy test against *Plutella xylostella* was carried out for the compounds shown in TABLE 10. All of the compounds demonstrated 80% or more of mortality rate against *Plutella xylostella*.

TABLE 10

| Compound No. | | | |
|---|---|---|---|
| 1-1 | 1-15 | 1-33 | 2-4 |
| 1-2 | 1-17 | 1-47 | 2-5 |
| 1-5 | 1-19 | 1-48 | 2-6 |
| 1-10 | 1-20 | 1-50 | 2-7 |
| 1-12 | 1-22 | 1-51 | |
| 1-14 | 1-24 | 1-52 | |

(Test Example 4) Efficacy Test Against *Aphis craccivor*

Cowpea plants were raised in No. 3 pots and the first true leaves were inoculated with *Aphis craccivora* nymphs. Emulsion (I) was diluted with water so that the concentration of the compound of the present invention reaches 125 ppm, followed by spraying the diluted liquid on the cowpea plants infested with *Aphis craccivora* nymphs. The cowpea plants were then placed in a thermostatic chamber with a temperature of 25° C. and a humidity of 60%. Life or death judgement was performed after 4 days were passed from the spraying, and the insect mortality rate of *Aphis craccivora* was calculated. The test was repeated twice.

Efficacy test against *Aphis craccivora* was carried out for the compounds shown in TABLE 11. All of the compounds demonstrated 80% or more of mortality rate against *Aphis craccivora*.

TABLE 11

| \multicolumn{4}{c}{Compound No.} | | | |
|---|---|---|---|
| 1-10 | 1-22 | 1-34 | 2-10 |
| 1-12 | 1-24 | 1-36 | 2-11 |
| 1-14 | 1-25 | 1-38 | 2-16 |
| 1-15 | 1-26 | 1-47 | 5-1 |
| 1-16 | 1-28 | 2-5 | 5-2 |
| 1-17 | 1-31 | 2-7 | 6-1 |
| 1-19 | 1-32 | 2-8 | |
| 1-20 | 1-33 | 2-9 | |

(Test Example 5) Efficacy Test Against *Bemisia tabaci*

Emulsion (I) was diluted with water so that the concentration of the compound of the present invention reaches 125 ppm, then the diluted liquid was sprayed on young seedlings of tomato, followed by air drying. On the day of the spraying, adult *Bemisia tabaci* were released to the seedlings so as to lay eggs. The number of parasitized larvae was calculated after 12 days were passed from the spraying. The efficacy of the compound was evaluated by the formula of prevention rate. The test was repeated twice.

Efficacy test against *Bemisia tabaci* was carried out for the compounds shown in TABLE 12. All of the compounds demonstrated 80% or more of prevention rate against *Bemisia tabaci*.

TABLE 12

| \multicolumn{4}{c}{Compound No.} | | | |
|---|---|---|---|
| 1-1 | 1-20 | 1-33 | 2-8 |
| 1-9 | 1-24 | 1-35 | 2-9 |
| 1-10 | 1-25 | 1-36 | |
| 1-12 | 1-26 | 1-38 | |
| 1-17 | 1-31 | 1-47 | |
| 1-19 | 1-32 | 2-5 | |

(Test Example 6) Efficacy Test Against *Phyllotreta striolata*

Emulsion (I) was diluted with water so that the compound of the present invention reaches 125 ppm to prepare a test solution. The above diluted solution was sprayed on bok choy seedlings (seventh true leaf development stage) planted in No. 3 pots. After air-drying, the bok choy seedlings were put in a plastic cup and 10 adult *Phyllotreta striolata* were released therein. The plastic cup was stored in a thermostatic chamber with a temperature of 25° C. and a humidity of 65%, and life or death judgment was performed 7 days after releasing *Phyllotreta triolata*, and the insect mortality rate was calculated by the formula. The test was repeated twice.

Efficacy test against adult *Phyllotreta striolata* was carried out for the compounds shown in TABLE 13. As a result, all the compounds demonstrated 80% or more of insect mortality rate against adult *Phyllotreta striolata*.

TABLE 13

| \multicolumn{4}{c}{Compound No.} | | | |
|---|---|---|---|
| 1-12 | 1-26 | 1-38 | 2-8 |
| 1-14 | 1-27 | 1-47 | 2-10 |
| 1-15 | 1-28 | 1-51 | 2-11 |
| 1-17 | 1-31 | 1-52 | 2-12 |

TABLE 13-continued

| \multicolumn{4}{c}{Compound No.} | | | |
|---|---|---|---|
| 1-19 | 1-32 | 2-5 | 2-16 |
| 1-24 | 1-33 | 2-6 | 6-1 |
| 1-25 | 1-36 | 2-7 | |

(Test Example 7) Efficacy Test Against *Musca domestica*

The compound of the present invention was diluted with acetone, followed by dropping to 1 g of cube sugar so that the concentration reaches to 100 ppm. The cube sugar was placed in a plastic cup and 10 adult female *Musca domestica* were released therein, followed by putting a lid on the cup. The cup was kept at 25° C., and life or death judgement was performed after 24 hours was passed from the releasing of *Musca domestica*, and the insect mortality rate was calculated by the formula. The test was repeated twice.

The efficacy test against *Musca domestica* was carried out for Compounds 1-12, 1-19, 1-24. The insect mortality rates against the adult female *Musca domestica* were 80% or more.

(Test Example 8) Efficacy Test Against *Culex pipiens*

Emulsion (I) was diluted with water so that the concentration of the compound of the present invention reaches 2 ppm to prepare a chemical solution for test. 20 first-instar larvae of *Culex pipiens* were released into 100 ml of the chemical solution for test, then the number of dead insects was calculated after 1 day was passed, and the insect mortality rate was calculated by the formula. The test was repeated twice.

The efficacy test against the first-instar larvae of *Culex pipiens* was carried out for Compounds 1-12, 1-14, 1-19, 1-24. All of the compounds demonstrated 100% of insect mortality rate against the first-instar larvae of *Culex pipiens*.

(Test Example 9) Efficacy Test Against *Pseudaletia Separate* (Seed Treatment)

0.1 g of each compound of the present invention was diluted with 2 ml of acetone to prepare a chemical solutions for test. 10 g of wheat seeds was added to the chemical solution for test and air dried, followed by seedling 100 seeds in a planter. After keeping the planter in a warm room with a temperature of 25° C. for 7 days, 100 first-instar larvae of *Pseudaletia* separate were released in the planter. The planter was kept in a warm room with a temperature of 25° C., the number of surviving *Pseudaletia* separate was investigated after 3 days were passed, and the prevention rate was calculated by the formula. The test was repeated twice.

The efficacy test against the first-instar larvae of *Pseudaletia* separate was carried out for Compounds 1-15, 1-24, 1-33. As a result, all of the compounds demonstrated 80% or more of prevention rate against the first-instar larvae of *Pseudaletia* separate.

(Test Example 10) Efficacy Test Against *Rhopalosiphum padi* (Seed Treatment)

0.1 g of each compound of the present invention was diluted with 2 ml of acetone to prepare chemical solutions for test. 10 g of wheat seeds was added to the chemical solution for test and air dried, followed by seedling 100 seeds in a planter. After keeping the planter in a warm room with a temperature of 25° C. for 7 days, 50 adult *Rhopalosiphum padi* were released in the planter. The number of surviving parasitized *Rhopalosiphum padi* was investigated after 6 days were passed, and the prevention rate was calculated by the formula. The test was repeated twice.

The efficacy test against *Rhopalosiphum padi* was carried out for Compound 1-33. As a result, the prevention rate against *Rhopalosiphum padi* was 80% or more.

(Test Example 11) Feeding Effect Test Against *Ornithodorus moubata*

A DMSO solution of the compound of the present invention was mixed with a defibrin blood of sheep to obtain a mixed solution with a concentration of 10 ppm. 2 ml of this mixed solution was placed in a container and capped with a parafilm membrane. Then, 20 third-nymphs of *Ornithodorus moubata* ere released to suck the blood through the parafilm membrane for about 30 minutes. Then, the nymphs were transferred to a storage container and incubated in a thermostatic chamber with a temperature of 28° C. and a humidity of 80%, and life or death judgement and developmental stage-investigation was performed 14 days after the blood sucking. The test was repeated twice.

The feeding effect test against *Ornithodorus moubata* was carried out for compound 1-12, and it showed an insect mortality rate of 90% or more.

(Test Example 12) Contact Effect Test on *Rhipicephalus microplus*

A DMSO solution of the compound of the present invention was diluted with water to obtain a test solution with a concentration of 100 ppm. This chemical solution was dropped into a container containing 20 *Rhipicephalus microplus* larvae, and then incubated in a thermostatic chamber with a temperature of 28° C. and a humidity of 80%. Life or death judgement was performed on the larvae 24 hours after the chemical treatment. The test was repeated twice.

The contact effect test against *Rhipicephalus microplus* was carried out for compound 1-12, and it showed an insect mortality rate of 90% or more.

(Test Example 13) Contact/Feeding Effect Test on *Lucilia cuprina* Larvae

A DMSO solution of the compound of the present invention was mixed with horse meat to obtain a mixture with a concentration of 1000 ppm. 20 *Lucilia cuprina* larvae were introduced into a test tube with the mixture. The tube was incubated in a thermostatic chamber with a temperature of 28° C. and a humidity of 80%, and life and death judgement was performed on the larvae 48 hours after the start of the test. The test was repeated twice.

The contact/feeding effect test against *Lucilia cuprina* larvae was carried out for compound 1-12, and it showed an insect mortality rate of 90% or more.

(Test Example 14) Contact/Feeding Effect Test on *Aedes aegypti* Larvae

A DMSO solution of the compound of the present invention was diluted with water to obtain a diluted solution with a concentration of 100 ppm. 10 first-instar larvae of *Aedes aegypti* were placed in each well of a 96-well microtiter plate together with breeding water, and 1/10 volume of the diluted solution with a concentration of 100 ppm was added so that the test was carried out at a final concentration of 10 ppm. The microtiter plate was incubated in a thermostatic chamber with a temperature of 28° C. and a humidity of 80%, and life or death judgement was performed on the larvae was investigated 48 hours after the chemical treatment. The test was repeated twice.

The contact/feeding effect test against *Aedes aegypti* larvae was carried out for compound No. 1-12, and it showed an insect mortality rate of 90% or more.

Since all of the compounds which were randomly selected from the compounds of the present invention demonstrated the above-mentioned effects, it can be understood that the compounds of the present invention, including the compounds which were unable to list in this description, can be used for controlling harmful organisms, particularly for controlling acari, insects or the like. It can also be understood that the compound of the present invention is effective for controlling parasites such as external parasites that are harmful to humans or animals.

INDUSTRIAL APPLICABILITY

The diarylazole compound of the present invention can control harmful organisms which are harmful to agricultural crops and cause problems in terms of hygiene. In particular, the diarylazole compound of the present invention can control various agricultural pests and acari effectively at a low concentration. Furthermore, the diarylazole compound of the present invention can effectively control external and internal parasites which are harmful to humans or animals. Therefore, the present invention is industrially useful.

The invention claimed is:
1. A compound represented by formula (I) or salt thereof

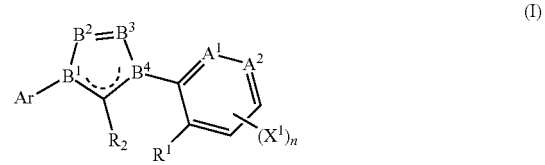

wherein in formula (I),
$A^1$ and $A^2$ each independently represent a carbon atom or a nitrogen atom, provided that $A^1$ and $A^2$ are not nitrogen atoms simultaneously;
$X^1$ represents an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, formyl group, an unsubstituted or substituted C1-6 alkylcarbonyl group, an unsubstituted or substituted C1-6 alkoxycarbonyl group, mercapto group, an unsubstituted or substituted C1-6 alkylthio group, an unsubstituted or substituted C1-6 alkylsulfinyl group, an unsubstituted or substituted C1-6 alkylsulfonyl group, an unsubstituted or substituted C3-8 cycloalkyl group, an unsubstituted or substituted C6-10 aryl group, an unsubstituted or substituted C6-10 aryloxy group, an unsubstituted or substituted 3- to 6-membered heterocyclyl group, an unsubstituted or substituted amino group, a halogeno group, a cyano group, or a nitro group;

n represents a number of $X^1$ and is an integer of 0 to 4, when n is 2 or more, $X^1$ may be the same as or different from each other;

$R^1$ is an unsubstituted or substituted C1-6 alkylthio group, an unsubstituted or substituted C1-6 alkylsulfinyl group, an unsubstituted or substituted C1-6 alkylsulfonyl group, an unsubstituted or a substituted or unsubstituted C1-6 alkylsulfonyloxy group, or a group represented by —S(=O)(=N—$R^a$)—$R^b$, here, $R^a$ and $R^b$ each independently represent an unsubstituted or substituted C1-6 alkyl group;

$B^1$ and $B^4$ each independently represent a carbon atom or a nitrogen atom, $B^2$ and $B^3$ each independently represent a nitrogen atom or $CR^3$, and when $B^1$ is a carbon atom, then $B^2$ is a nitrogen atom or $CR^3$, and $B^3$ and $B^4$ are nitrogen atoms, when $B^1$ is a nitrogen atom, then $B^2$ is a nitrogen atom, $B^3$ is a nitrogen atom or $CR^3$, and $B^4$ is a carbon atom;

$R^2$ represents a hydrogen atom, a halogeno group, a cyano group, an unsubstituted or substituted C1-6 alkyl group, an unsubstituted or substituted C2-6 alkenyl group, an unsubstituted or substituted C2-6 alkynyl group, a hydroxyl group, an unsubstituted or substituted C1-6 alkoxy group, formyl group, an unsubstituted or substituted C1-6 alkylcarbonyl group, an unsubstituted or substituted C1-6 alkoxycarbonyl group, an unsubstituted or substituted amino group, an unsubstituted or substituted C1-6 alkylsulfinyl group, an unsubstituted or substituted C1-6 alkylsulfonyl group, an unsubstituted or substituted C1-6 alkylsulfonyloxy group, or a group represented by —S(=O)(=N—$R^a$) —$R^b$, here, $R^a$ and $R^b$ each independently represent an unsubstituted or substituted C1-6 alkyl group;

$R^3$ represents a hydrogen atom or an unsubstituted or substituted C1-6 alkyl group; and Ar represents an unsubstituted or substituted C6-10 aryl group or an unsubstituted or substituted 5- to 6-membered heteroaryl group, the substituent of the substituted C6-10 aryl group and substituted 5- to 6-membered heteroaryl group for Ar is a C1-6 alkyl group, a C2-6 alkenyl group, a C2-6 alkynyl group, a C3-8 cycloalkyl group, a C6-10 aryl group, a C6-10 aryl C1-6 alkyl group, a 3- to 6-membered heterocyclyl group, a 3- to 6-membered heterocyclyl C1-6 alkyl group, a hydroxyl group, a C1-6 alkoxy group, a C2-6 alkenyloxy group, a C2-6 alkynyloxy group, a C6-10 aryloxy group, a C6-10 aryl C1-6 alkoxy group, a 5- to 6-membered heteroaryloxy group, a 5- to 6-membered heteroaryl C1-6 alkyloxy group, a formyl group, a C1-6 alkylcarbonyl group, a formyloxy group, a C1-6 alkylcarbonyloxy group, a C6-10 arylcarbonyl group, a C1-6 alkoxycarbonyl group, a C1-6 alkoxycarbonyloxy group, a carboxyl group, a halogeno group, a C1-6 haloalkyl group, a C2-6 haloalkenyl group, a C2-6 haloalkynyl group, a C1-6 haloalkoxy group, a C2-6 haloalkenyloxy group, a C1-6 haloalkylcarbonyl group, an amino group, a C1-6 alkyl-substituted amino group, a C6-10 arylamino group, a C6-10 aryl C1-6 alkylamino group, a formylamino group, a C1-6 alkylcarbonylamino group a mono C1-6 alkoxycarbonylamino group, a di-C1-6 alkoxycarbonylamino group, an imino C1-6 alkyl group, an unsubstituted or substituted N-hydroxyimino C1-6 alkyl group, an aminocarbonyloxy group, a C1-6 alkyl-substituted aminocarbonyloxy group, a mercapto group, a C1-6 alkylthio group, a C1-6 haloalkylthio group, a C6-10 arylthio group, a 5- to 6-membered heteroarylthio group, a C1-6 alkylsulfinyl group, a C1-6 haloalkylsulfinyl group, a C6-10 arylsulfinyl group, a 5- to 6-membered heteroarylsulfinyl group, a C1-6 alkylsulfonyl group, a C1-6 haloalkylsulfonyl group, a C6-10 arylsulfonyl group, a 5- to 6-membered heteroarylsulfonyl group, a C1-6 alkylsulfonyloxy group, a C1-6 haloalkylsulfonyloxy group, a tri-C1-6 alkyl-substituted silyl group, a tri-C6-10 aryl-substituted silyl group, a cyano group, or a nitro group.

2. The compound or salt thereof according to claim 1, wherein formula (I) is selected from formula (II) to formula (V)

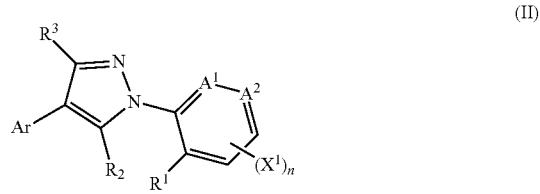

(II)

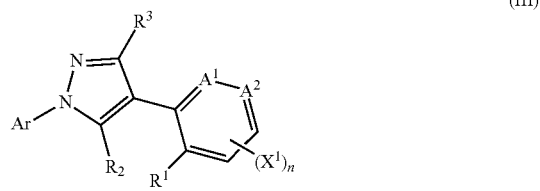

(III)

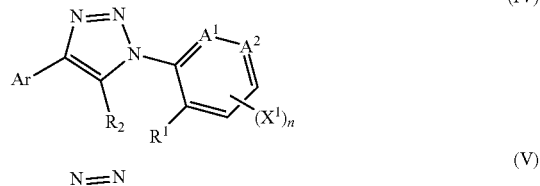

(IV)

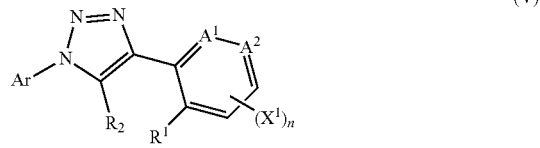

(V)

wherein, in formula (II), $A^1$, $A^2$, $X^1$, n, $R^1$, $R^2$, $R^3$ and Ar have the same meanings as those in formula (I).

3. A harmful organism control agent comprising at least one selected from the group consisting of the compounds and salts thereof defined in claim 1 as an active ingredient.

4. A harmful organism control agent comprising at least one selected from the group consisting of the compounds and salts thereof defined in claim 2 as an active ingredient.

5. An insecticide or acaricide comprising at least one selected from the group consisting of the compounds and salts thereof defined in claim 1 as an active ingredient.

6. An insecticide or acaricide comprising at least one selected from the group consisting of the compounds and salts thereof defined in claim 2 as an active ingredient.

7. An external parasite control agent comprising at least one selected from the group consisting of the compounds and salts thereof defined in claim 1 as an active ingredient.

8. An external parasite control agent comprising at least one selected from the group consisting of the compounds and salts thereof defined in claim 2 as an active ingredient.

9. An internal parasite control or extermination agent comprising at least one selected from the group consisting of the compounds and salts thereof defined in claim 1 as an active ingredient.

10. An internal parasite control or extermination agent comprising at least one selected from the group consisting of the compounds and salts thereof defined in claim 2 as an active ingredient.

11. A method for controlling a harmful organism comprising administering at least one selected from the group consisting of the compounds and salts thereof defined in claim 1 as an active ingredient.

12. A method for controlling a harmful organism comprising administering at least one selected from the group consisting of the compounds and salts thereof defined in claim 2 as an active ingredient.

13. A method for controlling an insecticide or acaricide comprising administering at least one selected from the group consisting of the compounds and salts thereof defined in claim 1 as an active ingredient.

14. A method for controlling an insecticide or acaricide comprising administering at least one selected from the group consisting of the compounds and salts thereof defined in claim 2 as an active ingredient.

15. A method for controlling an internal parasite comprising administering at least one selected from the group consisting of the compounds and salts thereof defined in claim 1 as an active ingredient.

16. A method for controlling an internal parasite comprising administering at least one selected from the group consisting of the compounds and salts thereof defined in claim 2 as an active ingredient.

* * * * *